(12) United States Patent
Bourget et al.

(10) Patent No.: US 11,291,843 B2
(45) Date of Patent: Apr. 5, 2022

(54) CHANGING ELECTRICAL STIMULATION

(71) Applicant: Medtronic, Inc., Minneapolis, MN (US)

(72) Inventors: Duane L. Bourget, Andover, MN (US); David E. Linde, Corcoran, MN (US); Robert Devine, New Brighton, MN (US); Benjamin P. Isaacson, Centerville, MN (US); Jeffrey Herron, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 623 days.

(21) Appl. No.: 16/213,578

(22) Filed: Dec. 7, 2018

(65) Prior Publication Data

US 2020/0179703 A1 Jun. 11, 2020

(51) Int. Cl.
*A61N 1/36* (2006.01)
*A61N 1/372* (2006.01)
*A61N 1/02* (2006.01)

(52) U.S. Cl.
CPC ......... *A61N 1/36192* (2013.01); *A61N 1/025* (2013.01); *A61N 1/36171* (2013.01); *A61N 1/36175* (2013.01); *A61N 1/36185* (2013.01); *A61N 1/37247* (2013.01)

(58) Field of Classification Search
CPC ............ A61N 1/36192; A61N 1/36171; A61N 1/37247; A61N 1/36175; A61N 1/36185; A61N 1/025
See application file for complete search history.

(56) References Cited

U.S. PATENT DOCUMENTS

| 9,259,587 | B2 | 2/2016 | Goetz et al. | |
|---|---|---|---|---|
| 11,007,368 | B2* | 5/2021 | Harkema | A61N 1/36171 |
| 2006/0200205 | A1* | 9/2006 | Haller | A61N 1/36146 |
| | | | | 607/41 |
| 2013/0289647 | A1* | 10/2013 | Bhadra | A61N 1/36007 |
| | | | | 607/41 |
| 2014/0277281 | A1* | 9/2014 | Grandhe | A61N 1/36153 |
| | | | | 607/59 |

* cited by examiner

*Primary Examiner* — Mallika D Fairchild
(74) *Attorney, Agent, or Firm* — Shumaker & Sieffert, P.A.

(57) ABSTRACT

Devices, systems, and techniques are described for transitioning between different groups of electrical stimulation programs. For example, a system may control delivery of second electrical stimulation defined by one or more second programs of a second group of stimulation programs on a time-interleaved basis with first electrical stimulation defined by one or more first programs of the first group of stimulation programs. The system may change a first ratio of the one or more first programs used to define the first electrical stimulation to the one or more second programs used to define the second electrical stimulation delivered within a first period of time to a second ratio of the one or more first programs used to define the first electrical stimulation to the one or more second programs used to define the second electrical stimulation delivered within a second period of time.

31 Claims, 10 Drawing Sheets

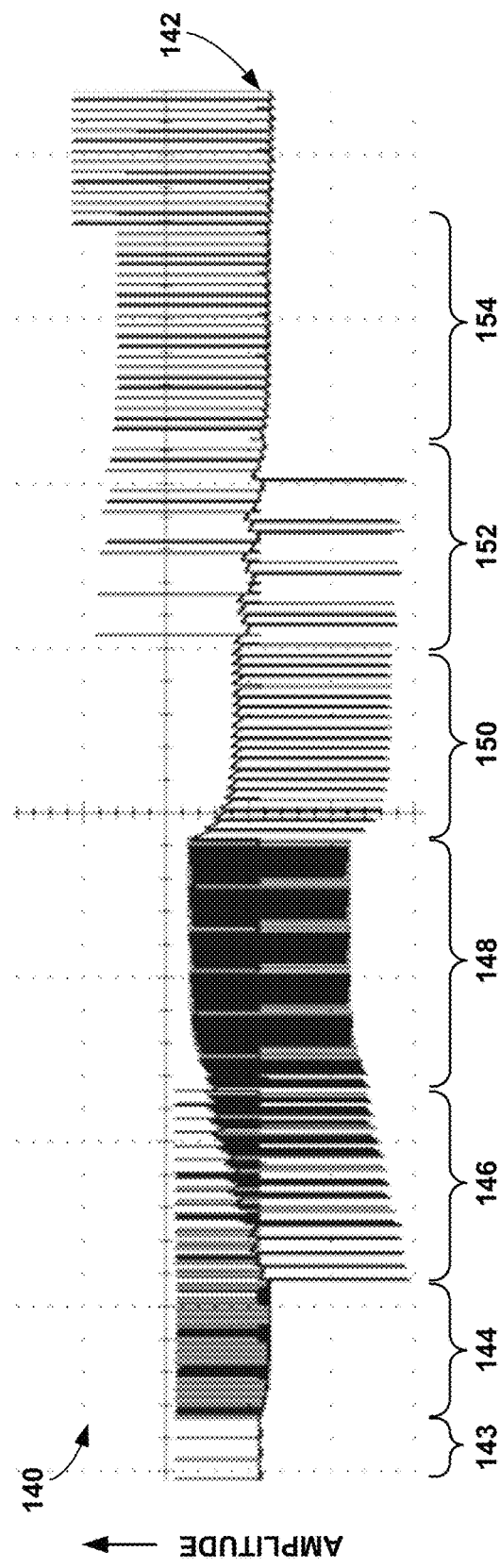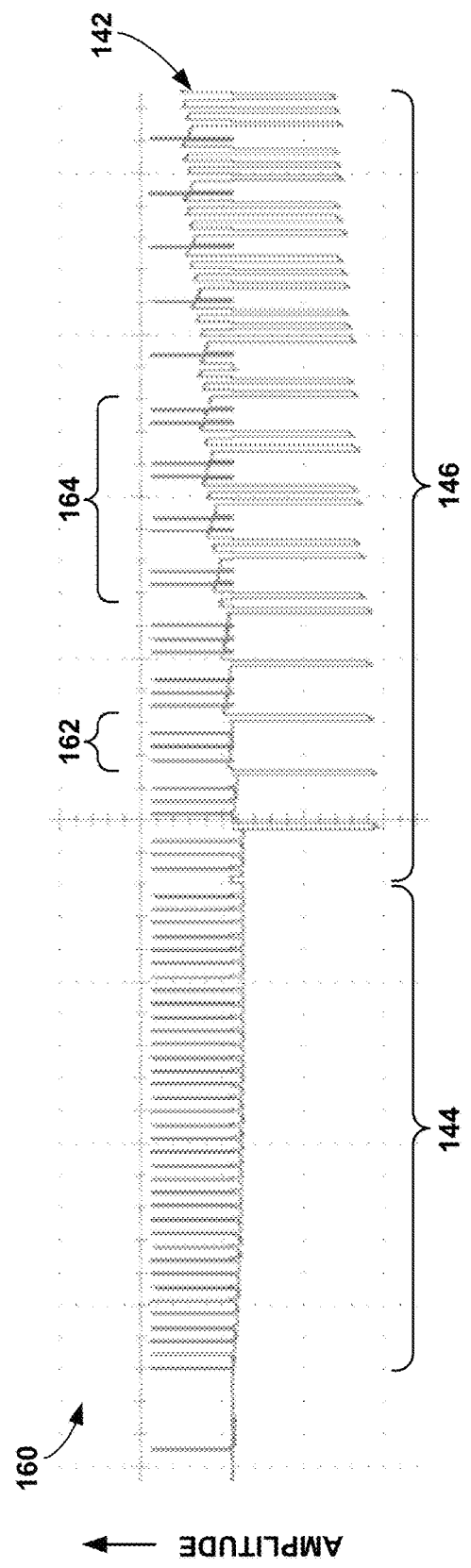

CHANGING ELECTRICAL STIMULATION

TECHNICAL FIELD

The invention relates to neurostimulation therapy and, more particularly, to changing parameters that define electrical stimulation therapy.

BACKGROUND

Implantable neurostimulators may be used to deliver neurostimulation therapy to patients to treat a variety of symptoms or conditions such as chronic pain, tremor, Parkinson's disease, epilepsy, urinary or fecal incontinence, sexual dysfunction, obesity, or gastroparesis. An implantable medical device may deliver neurostimulation therapy via leads that include electrodes located proximate to the spinal cord, pelvic nerves, stomach, or within the brain of a patient. In general, the implantable medical device delivers neurostimulation therapy in the form of electrical pulses.

A clinician selects values for a number of programmable parameters in order to define the neurostimulation therapy to be delivered to a patient. For example, the clinician selects an amplitude, which may be a current or voltage amplitude, and pulse width for a stimulation waveform to be delivered to the patient, as well as a rate at which the pulses are to be delivered to the patient. The clinician may also select particular electrodes within an electrode set to be used to deliver the pulses and the polarities of the selected electrodes. A group of parameter values may be referred to as a program in the sense that they drive the neurostimulation therapy to be delivered to the patient.

A neurostimulator may change stimulation programs for different reasons. For example, a neurostimulator may change programs to enable the patient to "screen" different programs for later use in defining therapy. In other examples, a neurostimulator may change between two or more programs during neurostimulation therapy in order to provide different types of therapy to the patient.

SUMMARY

In general, the disclosure is directed to devices, systems, and techniques for transitioning between different electrical stimulation programs. An electrical stimulation program may be defined by a set of stimulation parameter values, such as a value for one or more of a voltage or current amplitude, a pulse width, a pulse frequency, or an electrode combination. In addition, one or more stimulation programs may be used as a group, or set, of stimulation programs to define electrical stimulation over a period of time. When a device, e.g., an implantable medical device (IMD) such as an implantable neurostimulator, transitions from one set of stimulation programs to a different set of stimulation programs, the device can blend one or more of the stimulation programs from the first set of programs together with one or more of the stimulation programs from the second set of programs to deliver respective stimulation pulses during a transition period. In other words, the device may interleave, or interweave, one or more stimulation pulses defined by respective one or more stimulation programs of the first set of programs with one or more stimulation pulses defined by one or more stimulation programs of the second set of programs before the device fully transitions from stimulation defined by the first set of stimulation programs to stimulation defined by the second set of stimulation programs.

During the transition period, the IMD may change a ratio of the number of programs being delivered from the defined first set of programs to the number of programs being delivered from the defined second set of programs. For example, the IMD may deliver a high ratio of programs defined in the first set of programs to programs defined in the second set of programs during a first period of time within the transition period and deliver a low ratio of programs defined in the first set of programs to programs defined in the second set of programs during the second period of time within the transition period. In this manner, the IMD may iteratively increase the percentage of programs delivered from the second set of stimulation programs and iteratively decrease the percentage of programs delivered from the first set of stimulation programs during the transition period. This change in ratio of programs from the first and second sets of stimulation programs over a period of time may enable a less abrupt change in stimulation therapy perceived by the patient, for example.

In one example, a method includes controlling, by processing circuitry, delivery of first electrical stimulation defined by one or more first programs of a first group of stimulation programs, controlling, by the processing circuitry, delivery of second electrical stimulation defined by one or more second programs of a second group of stimulation programs on a time-interleaved basis with the first electrical stimulation defined by the one or more first programs of the first group of stimulation programs, wherein at least one program of the one or more first programs defines at least one stimulation parameter value different from at least one stimulation parameter value defined by at least one program of the one or more second programs, and changing, by the processing circuitry, a first ratio of the one or more first programs used to define the first electrical stimulation to the one or more second programs used to define the second electrical stimulation delivered within a first period of time to a second ratio of the one or more first programs used to define the first electrical stimulation to the one or more second programs used to define the second electrical stimulation delivered within a second period of time.

In another example, a system includes processing circuitry configured to control delivery of first electrical stimulation defined by one or more first programs of a first group of stimulation programs, control delivery of second electrical stimulation defined by one or more second programs of a second group of stimulation programs on a time-interleaved basis with the first electrical stimulation defined by the one or more first programs of the first group of stimulation programs, wherein at least one program of the one or more first programs defines at least one stimulation parameter value different from at least one stimulation parameter value defined by at least one program of the one or more second programs, and change a first ratio of the one or more first programs used to define the first electrical stimulation to the one or more second programs used to define the second electrical stimulation delivered within a first period of time to a second ratio of the one or more first programs used to define the first electrical stimulation to the one or more second programs used to define the second electrical stimulation delivered within a second period of time.

In another example, a non-transitory computer-readable medium comprising instructions that, when executed, cause processing circuitry to control delivery of first electrical stimulation defined by one or more first programs of a first group of stimulation programs, delivery of second electrical stimulation defined by one or more second programs of a second group of stimulation programs on a time-interleaved basis with the first electrical stimulation defined by the one or more first programs of the first group of stimulation programs, wherein at least one program of the one or more first programs defines at least one stimulation parameter value different from at least one stimulation parameter value defined by at least one program of the one or more second programs, and change a first ratio of the one or more first programs used to define the first electrical stimulation to the one or more second programs used to define the second electrical stimulation delivered within a first period of time to a second ratio of the one or more first programs used to define the first electrical stimulation to the one or more second programs used to define the second electrical stimulation delivered within a second period of time.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 8A and 8B are graphs of example blending of different stimulation programs from different groups of programs over transition periods.

DETAILED DESCRIPTION

Figure 1A:
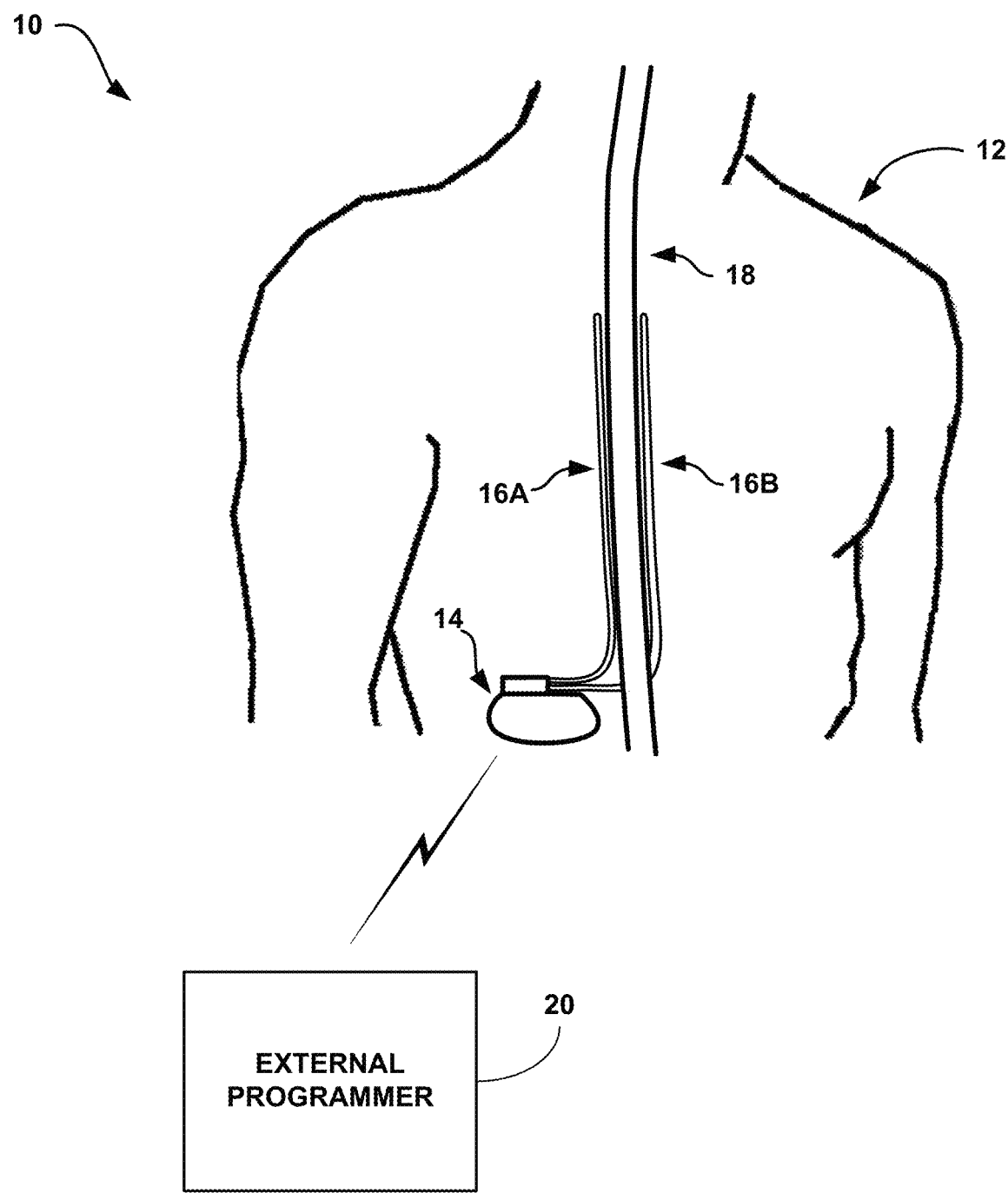
FIG. 1A is a conceptual diagram illustrating an example system for delivery and programming of neurostimulation therapy.

The disclosure describes examples of medical devices, systems, and techniques for transitioning between different groups of electrical stimulation programs. A medical device, such as an IMD or implantable neurostimulator, may be configured to deliver electrical stimulation therapy to a patient. The electrical stimulation may be defined by specific values for stimulation parameters such as a voltage or current amplitude, a pulse width, a pulse frequency, and/or an electrode combination. These specific values for these stimulation parameters may collectively be described as a stimulation program that defines the stimulation therapy. In addition, an IMD may deliver stimulation therapy according to a group of one or more stimulation programs. For example, pulses from respective programs within a single group of programs may be interleaved to deliver therapy according to each of the respective programs within the group.

The IMD may change between different groups of electrical stimulation programs during the course of electrical stimulation. For example, the IMD may store a plurality of different stimulation programs, wherein each program is associated with a respective group of programs, and deliver electrical stimulation according to the different stimulation programs to enable the patient to evaluate the efficacy of these stimulation programs. This process may be referred to as "screening" or "trialing" different electrical stimulation programs and/or different groups of programs. In other examples, the IMD may change between different groups of stimulation programs during delivery of therapy to the patient. For example, the IMD may change to a different group of stimulation programs configured to treat a different area (e.g., different location of pain or target a different nerve or tissue) or the IMD may change to a different stimulation program or group of stimulation programs that may be better suited to a different posture or activity of the patient.

In any instance of switching from one group of stimulation programs to another group of stimulation programs, the IMD may first reduce the amplitude of the stimulation pulses for the current group of stimulation programs to zero, e.g., 0 milliamps (mA) or 0 volts (V). The IMD may abruptly reduce the amplitude or ramp down the amplitude over time. Then, only after the amplitude of the pulses defined by the current group of stimulation programs are reduced to zero, the IMD may start delivering the pulses defined by the next group of stimulation programs. The IMD may similarly ramp up the amplitude of the pulses defined by the next group of stimulation programs. However, reducing pulse amplitudes to zero prior to moving to a new group of stimulation programs can increase the amount of time required to change from one group of stimulation programs to the new group of stimulation programs. For example, screening different groups of stimulation programs would take longer if stimulation amplitude needs to be reduced prior to changing to a new group of stimulation programs. The patient may not receive appropriate levels of stimulation therapy during this change. In some examples, requiring the IMD to reduce pulse amplitudes to zero prior to changing the group of stimulation programs may limit the types of group of stimulation programs (and the various different combinations of programs of number of different programs), and resulting therapies, that can be provided to the patient.

As described herein, an IMD, or other neurostimulation device, may transition between different groups, or sets, of electrical stimulation programs by interleaving pulses from a first group of stimulation programs with stimulation pulses from the second, or next, group of stimulation programs. These different stimulation programs within each group of stimulation programs may define different values for at least one stimulation parameter identified by the respective programs. For example, different programs may have different pulse amplitudes, pulse widths, pulse frequencies, and/or electrode combinations (e.g., different polarities and/or different electrodes used to deliver electrical stimulation). When the IMD transitions from the first, or current, group of stimulation programs to the second, or next, group of stimulation programs, the IMD is configured to blend pulses defined by the respective programs within each of the two groups of stimulation programs together during a transition period. The blending of pulses from each group of stimulation programs may be implemented as an interleaving or interweaving of one or more pulses defined by at least one stimulation program in the first group of programs with one or more pulses defined by at least one stimulation program of the second group of stimulation programs before the device fully transitions from the first group of stimulation programs to the second group of stimulation programs. Although two groups of stimulation programs are generally described as overlapping during this transition period, three or more groups of stimulation programs may be overlapped at the same time in other examples. A group of stimulation programs may include one, two, three, four, or more separate stimulation programs. Each stimulation program may have at least one stimulation parameter value different from the other stimulation programs. In this manner, the different programs may have some common parameter values (e.g., the same amplitude or pulse frequency) or no common parameter values.

During the transition period, the IMD may change a ratio of the number of programs from each group of programs used to define electrical stimulation pulses. For example, the IMD may, during a first period of time within the transition period, deliver pulses defined by more programs of the first group of programs than the second group of programs. Then, during a second period of time following the first period of time and within the same transition period, the IMD may deliver fewer pulses defined by programs of the first group of programs than the second group of programs. In some examples, the IMD may change the ratio three or more times during the transition period to affect the speed at which the IMD changes from one group of stimulation programs to the next group of stimulation programs. In this manner, the IMD may iteratively increase the percentage of pulses delivered from the second group of stimulation programs and iteratively decrease the percentage of pulses delivered from the first group of stimulation programs during the transition period. This change in ratio of pulses from the first and second groups of stimulation programs over the transition period may enable a less abrupt change in stimulation therapy perceived by the patient because the patient is continually receiving electrical stimulation pulses during the transition period. In some examples, by changing the ratios of programs from different groups of stimulation programs used to deliver interleaved pulses instead of ramping pulse amplitudes up and down, the patient may continue to receive stimulation pulses with amplitudes as intended by the respective stimulation programs. In this manner, blending stimulation programs during a transition period may provide improved therapy to a patient. However, in some examples, the IMD may ramp amplitudes up or down as pulses from new stimulation programs are introduced or pulses from current stimulation programs are removed, respectively.

The techniques described herein may be used during a programming test mode, e.g., within a clinic or outside a clinic, to shift between different groups of stimulation programs in an effort to identify efficacious programs, and groups of programs, for a patient who has been selected as a candidate for stimulation therapy. Also, the techniques may be used in a screening mode in which the patient is evaluated for chronic implantation of a stimulator. Additionally, the techniques may be used for changing between different groups of stimulation programs in an operational mode, i.e., in normal usage by the patient after programming of an implanted neurostimulator. In each case, the implanted stimulator may gradually shift from pulses defined by programs of a first group of stimulation programs to pulses defined by programs of a second group of stimulation programs in incremental steps by blending pulses from one or more programs from each group of stimulation programs together over a transition period.

In one example, the IMD may incrementally change the ratio of programs from each group of stimulation programs used to define stimulation pulses between different sets of time intervals, i.e., time slots or slots, delivered on a time-interleaved basis. Each time slot of a set of slots may include one or more pulses of stimulation energy defined by a single stimulation program. For example, in each of the first three time slots of a set of slots, one or more stimulation pulses are delivered according to a respective stimulation program of the first group of programs. In the fourth, and final, time slot of the set of slots, one or more stimulation pulses are delivered according to a stimulation program of a second group of programs. Then, the IMD may change the ratio of programs from each group of programs used for each time slot of the next set of slots. The IMD may, in each of the first two time slots of the second set of slots, deliver one or more stimulation pulses according to the respective programs of the first group of stimulation programs. In each of the third and fourth time slots of the second set of slots, the IMD may deliver one or more stimulation pulses according to the respective programs of the second group of stimulation programs. In this manner, the IMD is changing the ratio of the programs from the first and second group of stimulation programs that define the respective pulses delivered during one set of slots to the next set of slots. The IMD may continue changing the ratio of programs from each group of programs used to deliver pulses until the IMD is only delivering pulses defined by programs of the second group of stimulation programs during all time slots of a set of slots.

In some examples, the IMD may only deliver a single pulse in any one time slot. The IMD may determine the duration of time for each time slot according to the pulse frequency and/or the pulse width of the stimulation programs from the group of stimulation programs defining pulses for the transition period. In other examples, the IMD may blend pulses defined by programs from two or more different groups of stimulation programs over a transition period without using slots or sets of pulses.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal that may have a sinusoidal waveform or other continuous waveform.

FIG. 1A is a conceptual diagram illustrating an example system 10 for delivery and programming of neurostimulation therapy to patient 12. System 10 includes an implantable neurostimulator 14 (e.g., an example implantable medical device) that delivers neurostimulation therapy to patient 12 and a programmer 20 for programming implantable neurostimulator 14. Neurostimulator 14 delivers neurostimulation therapy to patient 12 via leads 16A and 16B (collectively "leads 16"). Leads 16 may, as shown in FIG. 1A, be implanted proximate to spinal cord 18 of patient 12 to deliver spinal cord stimulation (SCS) therapy to patient 12. Spinal cord stimulation may be used, for example, to reduce pain experienced by patient 12 (e.g., by providing paresthesia and/or blocking the transmission of nerve impulses). Although an implantable neurostimulator 14 is described for purposes of illustration, various embodiments of this disclosure also may be applicable to external neurostimulators that reside outside the patient's body and deliver stimulation therapy using one of more implanted leads deployed via a percutaneous port. Leads 16 may also be located at other nerve or tissue sites within patient 12. In addition, system 10 is not limited to spinal cord stimulation, and may be applicable to other electrical stimulation applications including pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, Parkinson's disease, epilepsy, urinary or fecal incontinence, sexual dysfunction, obesity, or gastroparesis. The IMD and/or leads may be constructed for these different applications in some examples. Moreover, in other examples, neurostimulator 14 may be configured to provide deep brain stimulation (DBS) as described with respect to FIG. 1B herein.

Neurostimulator 14 delivers neurostimulation therapy to patient 12 according to one or more neurostimulation therapy programs (e.g., a stimulation program). A neurostimulation therapy program may specify an electrode combination and values for a number of stimulation parameters associated with neurostimulation therapy delivered via the electrode combination. The stimulation parameters may include stimulation pulse voltage or current amplitude, pulse width, pulse rate, and other appropriate parameters such as duration or duty cycle. In some examples, stimulation parameters may also specify a burst frequency, a burst duration, burst pulse number, or any other defining characteristic of bursts (i.e., groups) of pulses that may be delivered by neurostimulator 14. Leads 16 each include one or more electrodes (not shown in FIG. 1A). Each program further specifies an electrode combination in terms of electrodes that have been selected to deliver pulses according to the program and the polarities of the selected electrodes. In this manner, the electrode combination may specify which specific electrodes of the possible electrodes carried by leads 16 will be used to deliver electrical stimulation according to the stimulation program. Neurostimulator 14 may also deliver stimulation according to a group of one or more stimulation programs, where each program defines at least one different parameter value.

Two example parameters of therapy are the electrode combination and the stimulation amplitude. The selection of electrodes determines which tissues are stimulated and, therefore, which physiological effects are perceived. Stimulation voltage or current amplitude determines the intensity and the extent of those effects. These electrode combination and stimulation amplitude settings are tightly coupled. A comfortable stimulation amplitude for one electrode combination might be uncomfortable or imperceptible for a second electrode combination. Similarly, the combination of amplitude and pulse width may contribute to a total electrical charge delivered to patient 12 and the perceived "intensity" of stimulation perceived by patient 12.

Programmer 20 provides a programming interface that provides information to, and can receive information from, neurostimulation 14. For example, programmer 20 may deliver the stimulation programs to neurostimulation 14 and/or instructions regarding how neurostimulator 14 should blend programs from different groups of stimulation programs when transitioning from one group of stimulation programs to another group of stimulation programs. Blending pulses from the programs of each group of stimulation programs and changing the ratio of programs used to define pulses from each group of stimulation programs over time, may allow neurostimulator 14 to change from one group to another group in a gradual manner that allows the change in stimulation to be imperceptible or at least comfortable for the patient. As described in more detail herein, the blending of groups may involve iteratively adjusting the ratio of programs from the current group of stimulation programs to the programs of the next group of stimulation programs. Accordingly, the blended pulses from respective programs from each group of stimulation programs may be interleaved in time during the transition period from the current group to the next group.

Neurostimulator 14 may deliver neurostimulation therapy to patient 12 according to a plurality of programs (e.g., a group of programs) for a single symptom area, such as a number of leg pain programs. Neurostimulator 14 may have different program parameters for each of the leg pain programs based on a position of patient 12, an activity rate of patient 12, or other patient parameters. For example, neurostimulator 14 may deliver neurostimulation therapy to patient 12 during a first leg pain program using a first electrode combination when patient 12 is lying down and deliver neurostimulation therapy to patient 12 using a second leg pain program via a second electrode combination when patient 12 is standing. In some embodiments, patient 12 may use programmer 20 to input parameters to indicate posture changes, such as sitting, standing, or lying down. In other embodiments, neurostimulator 14 may include an orientation device to automatically determine the posture and/or activity of patient 12. The orientation device may be similar to, or include, one or more accelerometers and/or gyroscopes. In some examples, groups of programs may define pulses targeted to provide different effects to the same area of the patient 12 or various effects to different locations (e.g., a group may have programs selected for different respective areas such as each leg and a back).

A programmer user, such as the clinician or patient 12, may use programmer 20 to program neurostimulation therapy for patient 12. In particular, the user may use programmer 20 to create neurostimulation therapy programs (e.g., define values for one or more stimulation parameters), groups of therapy programs, and update the neurostimulation therapy programs and groups used to deliver pulses by neurostimulator 14. As part of the program creation process, programmer 20 may enable the user to evaluate the different programs that neurostimulator 14 used to deliver neurostimulation therapy that is desirable in terms of, for example, symptom relief, coverage area relative to symptom area, and lack of side effects. Programmer 20 may also allow the user to evaluate programs that enable neurostimulator 14 to deliver effective neurostimulation therapy with desirable device performance characteristics, e.g., low battery consumption. Programmer 20 controls neurostimulator 14, e.g., by instructions delivered via wireless telemetry, but wired communication may be used in other examples. Programmer 20 may also enable the user to group two or more programs together into a single group of stimulation programs.

During clinic evaluation of different programs for programming of neurostimulator 14, the change between groups of stimulation programs may proceeds under user control. The changes in the ratio of programs used to define pulses from each group of stimulation programs over the transition period may proceed in an automated fashion based on a predetermined schedule and/or input from one or more sensors. In one example, each incremental change in the ratio of programs during the transition period may be contingent on input from the user. For example, programmer 20 may wait for the user to actuate an input device before performing the next incremental change in the ratio of programs from each group. In another embodiment, programmer 20 may proceed through the incremental changes in ratio of programs automatically unless it receives input from the user. For example, the user may control a dead man switch, and programmer 20 may cease the incremental change in ratio of programs from each group upon deactivation of the dead man switch. In some examples, programmer 20 may receive input from the user that controls reversion to pulses only defined by the current group instead of the next group that was defining at least some pulses to the ratio of programs during the transition period. These controls of programmer 20 may be in addition to amplitude, pulse width and rate adjustment controls, and may be operated by a physician or patient 12. Most, if not all of these parameter controls may be provided by a clinician programmer version of programmer 20. However, a patient programmer version of programmer 20 may limit patient access to at least some of these parameter values, such as pulse width or pulse frequency. For example, a patient programmer may limit the patient control to selecting one or more predetermined programs and amplitude of the pulses from each program.

Additionally, programmer 20 may provide the user with the ability to control the overall intensity of the stimulation. Programmer 20 may, for example, include an input mechanism that allows the user to increase or decrease the intensity of the stimulation at any point during the change process to maintain comfortable sensations. In response to receiving input to increase or decrease the intensity of the stimulation, programmer 20 may adjust the intensity of one or both of the currently active programs as well as the target amplitude towards which the stimulation amplitude is progressing. Since intensity may be a combination of amplitude and pulse width, in some examples, the intensity control may adjust one or both of these parameters in response to receive appropriate input from the patient.

As described herein, system 10 may include processing circuitry configured to perform several features. The processing circuitry may be housed by programmer 20, neurostimulator 14, or a combination of programmer 20 and neurostimulator 14, in some examples. The processing circuitry may be configured to control delivery of first electrical stimulation defined by one or more first programs of a first group of stimulation programs and control delivery of second electrical stimulation on a time-interleaved basis with the first electrical stimulation, the second electrical stimulation being defined by one or more second programs of a second group of stimulation programs. For example, the processing circuitry may control an implantable medical device, such as neurostimulator 14, to deliver pulses of the first and second electrical stimulation on the time-interleaved basis to provide stimulation pulses "blended" from the first group of stimulation programs and from a second group of stimulation programs, wherein each group of stimulation programs differs by at least one program with at least one different parameter value from the programs of the other group. Generally, two different group of stimulation programs have at least one different program between them. In other words, each group of stimulation programs may be different from each other because at least one program of one group defines at least one stimulation parameter value that is different from at least one program from the other group. However, in practice, two different groups of stimulation programs have several different programs between then. In this manner, a first value of at least one parameter of a program in the first group of stimulation programs is different than a second value of at least one parameter of a program in the second group of stimulation programs. It is noted that two different programs, in the same or different group, may have one or more parameters of the same value. For example, two programs may have the same pulse amplitude values and pulse frequencies, but the two programs may be different because they have different pulse width values.

The processing circuitry may be configured to change a first ratio of the one or more first programs used to define the first electrical stimulation to the one or more second programs used to define the second electrical stimulation delivered within a first period of time to a second ratio of the one or more first programs used to define the first electrical stimulation to the one or more second programs used to define the second electrical stimulation delivered within a second period of time. In this manner, the first ratio of programs is different than the second ratio of programs in order to change the ratio of first programs to the second ratio of programs. The ratio of programs is described herein, the ratio refers to the ratio of programs used to define respective pulses within a period of time. For example, each pulse delivered in a period of time may be defined by a respective program from one or more groups of programs. Therefore, if more programs from a first group of programs are used in a period of time than programs from a second group of programs, the period of time includes more pulses defined by programs of the first group of programs than pulses defined by programs of the second group of programs. The first and second periods of time may be considered to be within the transition period during which pulses from each of the two groups of programs are delivered, for example. The processing circuitry may continue to change the ratios of the programs from the first group to the programs of the second group until only electrical stimulation pulses defined by the programs of the second group are being delivered because the processing circuitry has fully changed from the first group of programs to the second group of programs. Although a change to the ratio of programs from each group of programs is described herein, this change may similarly refer to a change in the ratio of pulses defined by programs from the first group to pulses defined by programs from the second group.

In some examples, the processing circuitry may change the first ratio of programs to the second ratio of programs within the transition period by increasing a number, or an amount, of the second group of stimulation programs used define pulses delivered during the second period of time as compared to the first period of time. In other words, the processing circuitry may increase the number of pulses defined by one or more programs of the next group of stimulation programs such that the ratio of programs becomes increasingly weighted with programs from the next group of stimulation programs. In some examples, the increased number of programs from the next group of stimulation programs occurs without a corresponding decrease in programs from the current group of stimulation programs. In some examples, in addition to increasing the number of second programs from the second group during the second period of time, the processing circuitry may change the first ratio by decreasing the number of the first programs from the first group that define stimulation pulses delivered during the second period of time compared to the first period of time. However, in other examples, the processing circuitry may change the first ratio of the first programs to the second programs delivered within the first period of time to the second ratio of the first programs to the second programs delivered within the second period of time by decreasing the number of the first programs delivered during the second period of time as compared to the first period of time and without also increasing the number of the second programs during the second period of time as compared to the first period of time. In this manner, the processing circuitry may change the ratio of programs from two different programs that define pulses by decreasing the number of programs from the first group of stimulation programs and/or increasing the number of programs from the second group of stimulation programs that define pulses during a certain period of time within the transition period.

In some examples, the processing circuitry may iteratively change the ratios of programs that used to deliver pulses on a time-interleaved basis during different periods within the transition period. In each iterative change, the ratio may be changed to increase the number of programs from the next group of stimulation programs with respect to the programs from the current group of stimulation programs. This iterative change in ratios of programs may continue until only pulses from programs from the next group of stimulation programs are being delivered, i.e., the processing circuitry has completely changed from the current group of stimulation programs to the next group of stimulation programs. In some examples, the change in the ratios may be linear from the beginning to the end of the transition period. In other examples, the change in ratios may be smaller at the beginning of the transition period, larger during the middle of the transition period, and smaller again at the end of the transition period. The processing circuitry may deliver any change in rations over the transition period that may be selected based on the type of stimulation of each program, or group of stimulation programs, involved in the change, differences between the values of one or more parameters of each program or group of stimulation programs, and/or patient preferences (e.g., some patients may be more sensitive to changes in stimulation than other patients).

The electrical pulses within each period of the transition period may be ordered in a particular way. For example, the processing circuitry may iteratively replace more programs from the current group of stimulation programs that define pulses at the end of each successive period with one or more programs from the next group of stimulation programs. Alternatively, the processing circuitry may iteratively replace more programs from the current group of stimulation programs that define pulses at the beginning of each successive period with one or more programs from the next group of stimulation programs. In other examples, the processing circuitry may iteratively replace more programs of the current group of stimulation programs that define pulses at random locations within the period of each successive period with one or more programs from the next group of stimulation programs.

In some examples, the processing circuitry is configured to change a first order of the pulses defined by the first electrical stimulation programs from the first group of stimulation programs and pulses defined by the second electrical stimulation programs from the second group of stimulation programs delivered within the first period of time to a second order of the pulses defined by the first electrical stimulation programs and pulses defined by the second electrical stimulation programs delivered within a third period of time, all within the transition period. In other words, in some examples, the processing circuitry may not change the ratio of programs from each group of stimulation programs from one period to the next within the transition period, but the processing circuitry may instead change the order at which the pulses from the respective programs of the first and second group of stimulation programs from the previous period to the next period within the transition period. In other examples, the processing circuitry may change the order of pulses defined by respective programs from the different group of stimulation programs and the ratio of the programs from the different group of stimulation programs from one period of time to the next period of time within the transition period. By way of these different paradigms for changing stimulation from one group of stimulation programs to another group of stimulation programs, the processing circuitry may have flexibility to customize the blending of pulses from different group of stimulation programs to accommodate differences between patients and variations between the type of parameters changed between the different programs from two different groups of stimulation programs that are part of the blend.

Although the transition between two different groups of stimulation programs are generally described herein as an example, the system may use these types of transitions to change between several different groups of stimulation programs. For example, in addition to first electrical stimulation from programs of a first group of stimulation programs, the processing circuitry may control delivery of third electrical stimulation (e.g., defined by one or more programs of a third group of stimulation programs) on the time-interleaved basis with the first electrical stimulation and the second electrical stimulation within at least one of the first period of time or the second period of time of the transition period. In this manner, pulses from three or more groups of stimulation programs may be interleaved together to change between groups of stimulation programs.

Figure 4:
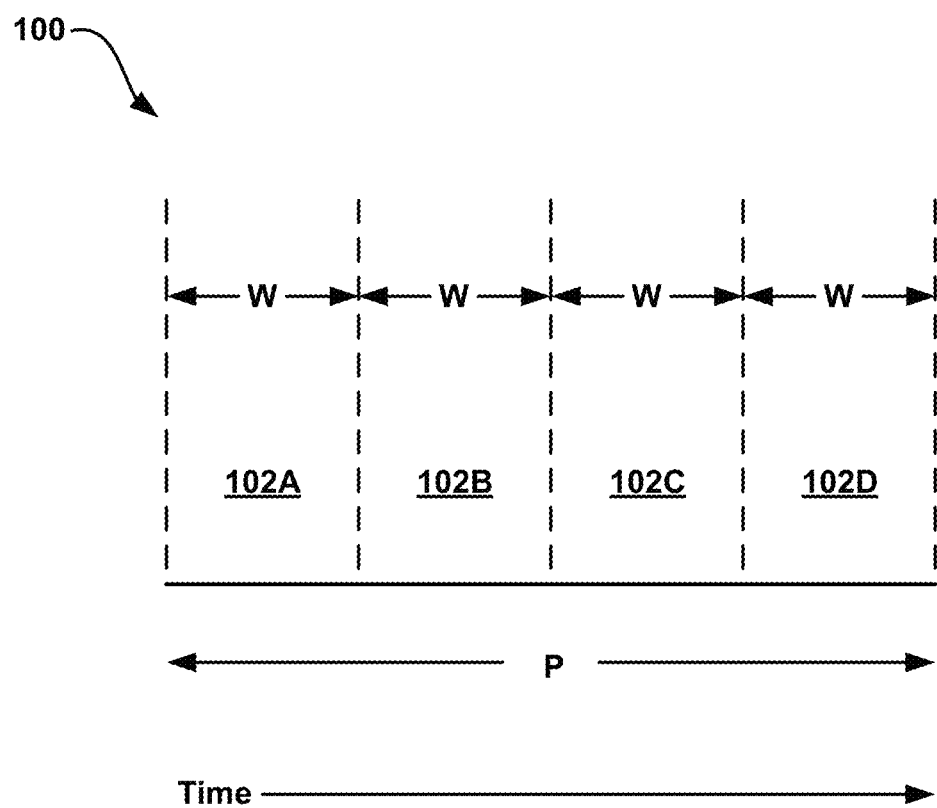
FIG. 4 is a conceptual diagram illustrating an example set of time slots within which a respective stimulation pulse from a respective stimulation program may be delivered.

In some examples, each period within the transition period may be described as having a set of time slots (e.g., as shown in the example of FIG. 4). For example, each of the first period of time and the second period of time of a transition period may include a plurality of time slots. Each time slot of the plurality of time slots may be configured to contain up to a single stimulation pulse from one of at least the first electrical stimulation of a program from a first group of stimulation programs or the second electrical stimulation of a program from a second group of stimulation programs. Each set of time slots may include three, four, five, six, seven, eight, or more individual time slots. In some examples, the duration of each time slot of the plurality of time slots correspond to a common pulse rate period shared between the first stimulation pulses of the first group of stimulation programs and the second stimulation pulses of the second group of stimulation programs. For example, the common pulse rate period may be chosen to be a common multiple of the pulses defined by the programs of the first and second groups of stimulation programs that allows the duration of each time slot to accommodate pulses from any program from the first or second groups of stimulation programs at the defined pulse frequency, or pulse rate, from each respective group. In one example, the duration of each time slot may have a duration of 20 milliseconds (ms) to accommodate the pulse frequency of 50 Hz defined by programs of the first group of stimulation programs and the pulse frequency of 25 Hz defined by programs from the second group of stimulation programs.

In some examples, each set of time slots includes at least four time slots having equal lengths, or durations. However, in other examples, time slots within a set of time slots may have different durations, which may be selected based on the pulse width and/or pulse frequency of one or more programs. As described herein, a single stimulation pulse refers to a stimulation phase and a recharge phase. In this manner, each time slot may include both the stimulation phase and the recharge phase. However, in other examples, each time slot may be configured to include only the stimulation phase or a recharge phase. In some examples, a single recharge phase may be delivered after two or more stimulation phases delivered in respective time slots, such that the single recharge phase is configured to restore charge for both of the two or more stimulation phases.

As described herein, the processing circuitry is configured to control the delivery of the first electrical stimulation from a first group of stimulation programs by controlling delivery of at least one first electrical stimulation pulse within the second period of time of the transition period and controlling the delivery of the second electrical stimulation from a second group of stimulation programs by controlling delivery of at least one second electrical stimulation pulse within the second period of time of the transition period. In other examples, the processing circuitry is configured to control the delivery of the second electrical stimulation pulses defined by one or more second programs of a second group of stimulation programs on the time-interleaved basis with the first electrical stimulation pulses defined by one or more first programs of a first group of stimulation programs by controlling the delivery of a first set of one or more first electrical stimulation pulses alternating with a second set of one or more second electrical stimulation pulses. In this manner, as few as one pulse, but two or more pulses, from one program of one group of stimulation programs may be interleaved with as few as one pulse, or two or more pulses, from another program of a different group of stimulation programs.

The processing circuitry may control a stimulation generator of neurostimulator 14 to generate and deliver each of the pulses, for example. As discussed herein, the parameters of each stimulation program may include at least one of an amplitude, a pulse rate, a pulse width, an electrode combination, or an electrode polarity. Some programs may define values for all of these parameters. However, in other examples, a program may only define as few as one value for a single parameter when other parameters are common, or unchanged, between two or more programs.

Figure 1B:
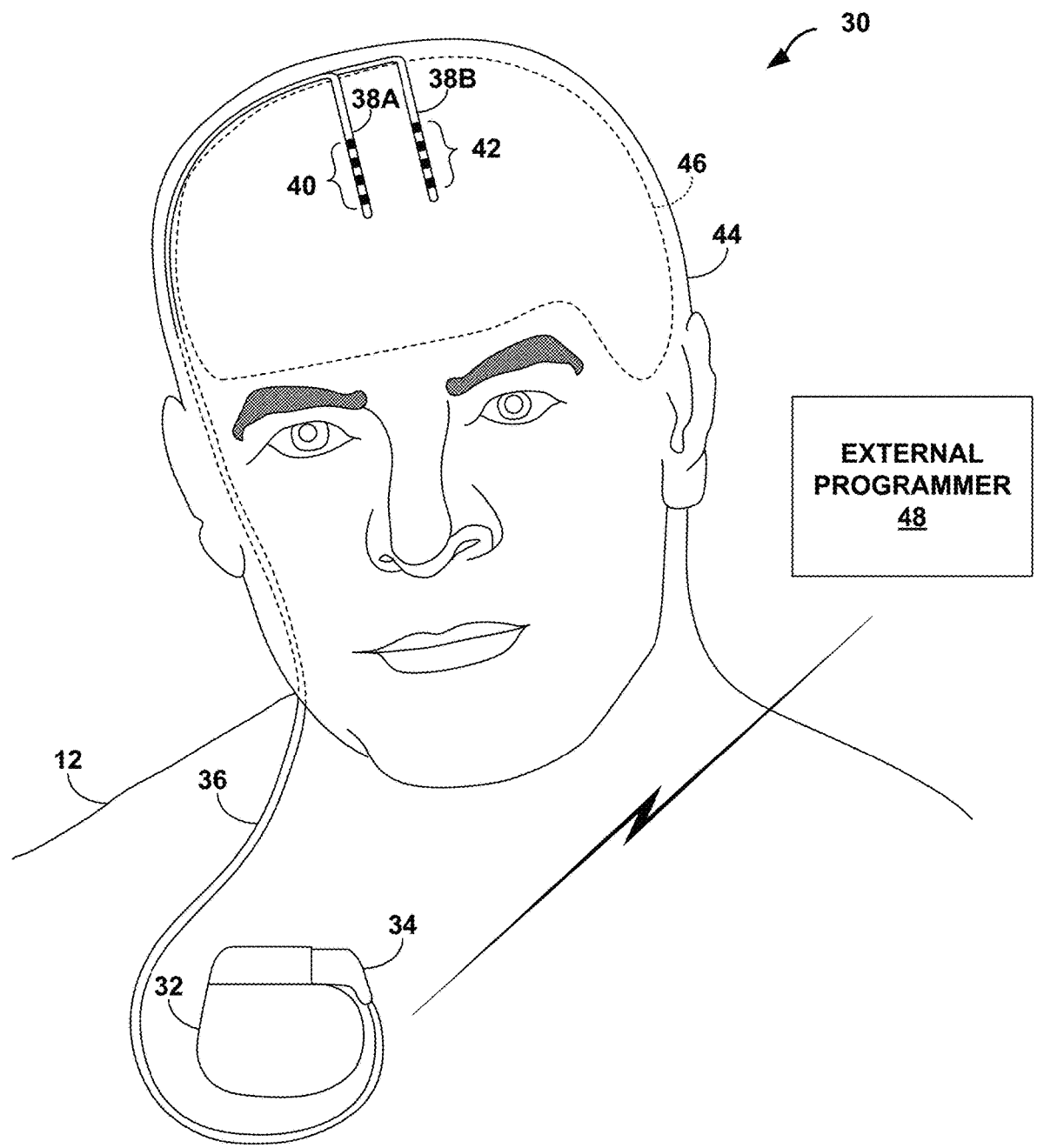
FIG. 1B is a conceptual diagram illustrating an example system for delivery and programming of deep brain stimulation therapy.

The disclosure is not limited to the combination of leads 16 shown in FIG. 1A. For example, system 10 may include only a single lead or more than two leads implanted proximate spinal cord 18. Furthermore, the examples herein are not limited to the delivery of SCS therapy. For example, one or more leads 16 may extend from neurostimulator 14 to the brain (not shown, but possibly as shown in FIG. 1B) of patient 12, and neurostimulator 14 may deliver deep brain stimulation (DBS) therapy to patient 12 to treat tremor or epilepsy (as shown in FIG. 1B). As further examples, one or more leads 16 may be implanted proximate to the pelvic nerves (not shown) or stomach (not shown), and neurostimulator 14 may deliver neurostimulation therapy to treat incontinence or gastroparesis.

While programmer 20 of FIG. 1A and other programmers described herein are described as individual units, a programmer may instead be shown on a touch screen, or other display, of a larger computer. In other words, programmer 20, or other programmers, may be virtual programmers that allow a user to interact with them through the touch screen or other pointing device. Operation of a virtual programmer may be substantially similar to an individual, or standalone, programmer.

FIG. 1B is a conceptual diagram illustrating an example system 30 for delivery and programming of deep brain stimulation therapy. As shown in FIG. 1B, system 30 that includes implantable medical device (IMD) 32 configured to deliver deep brain stimulation to patient 12. System 30 may be similar to system 10 of FIG. 1A, but system 30 is directed to DBS therapy. Patient 12 may be similar or different from patient 12 of FIG. 1A. System 30 may be configured to treat a patient condition, such as a movement disorder, neurodegenerative impairment, a mood disorder or a seizure disorder of patient 12. Patient 12 ordinarily will be a human patient. In some cases, however, therapy system 30 may be applied to other mammalian or non-mammalian, non-human patients. While movement disorders and neurodegenerative impairment are primarily referred to herein, in other examples, therapy system 30 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 30 includes medical device programmer 48, implantable medical device (IMD) 32, lead extension 36, and leads 38A and 38B with respective sets of electrodes 40, 42. In the example shown in FIG. 1B, electrodes 40, 42 of leads 38A, 38B are positioned to deliver electrical stimulation to a tissue site within brain 46, such as a deep brain site under the dura mater of brain 46 of patient 12. In some examples, delivery of stimulation to one or more regions of brain 46, such as the subthalamic nucleus, globus pallidus or thalamus, may be an effective treatment to manage movement disorders, such as Parkinson's disease. Electrodes 40, 42 are also positioned to sense bioelectrical brain signals within brain 46 of patient 12. In some examples, some of electrodes 40, 42 may be configured to sense bioelectrical brain signals and others of electrodes 40, 42 may be configured to deliver electrical stimulation to brain 46. In other examples, all of electrodes 40, 42 are configured to both sense bioelectrical brain signals and deliver electrical stimulation to brain 46.

IMD 32, which may be similar to neurostimulator 14, includes a therapy module that includes a stimulation generator that generates and delivers electrical stimulation therapy to patient 12 via a subset of electrodes 40, 42 of leads 38A and 38B, respectively. The subset of electrodes 40, 42 that are used to deliver electrical stimulation to patient 12, and, in some cases, the polarity of the subset of electrodes 40, 42, may be referred to as a stimulation electrode combination.

Electrical stimulation generated by IMD 32 may be configured to manage a variety of disorders and conditions. In some examples, the stimulation generator of IMD 32 is configured to generate and deliver electrical pulses to patient 12 via electrodes of a selected stimulation electrode combination. However, in other examples, the stimulation generator of IMD 32 may be configured to generate and deliver a continuous wave signal, e.g., a sine wave or triangle wave. In either case, a signal generator within IMD 32 may generate the electrical stimulation therapy for DBS according to a therapy program that is selected at that given time in therapy. In examples in which IMD 32 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As previously indicated, the stimulation electrode combination may indicate the specific electrodes 40, 42 that are selected to deliver stimulation signals to tissue of patient 12 and the respective polarity of the selected electrodes. In addition, IMD 32 may blend pulses from different programs when switching between programs.

IMD 32 may be implanted within a subcutaneous pocket above the clavicle, or, alternatively, the abdomen, back or buttocks of patient 12, on or within cranium 32 or at any other suitable site within patient 12. Generally, IMD 32 is constructed of a biocompatible material that resists corrosion and degradation from bodily fluids. IMD 32 may comprise a hermetic housing to substantially enclose components, such as a processor, therapy module, and memory.

As shown in FIG. 1B, implanted lead extension 36 is coupled to IMD 32 via connector 34 (also referred to as a connector block or a header of IMD 32). In the example of FIG. 1B, lead extension 36 traverses from the implant site of IMD 32 and along the neck of patient 12 to cranium 44 of patient 12 to access brain 46. In the example shown in FIG. 1B, leads 38A and 38B (collectively "leads 38") are implanted within the right and left hemispheres, respectively, of patient 12 in order deliver electrical stimulation to one or more regions of brain 46, which may be selected based on the patient condition or disorder controlled by therapy system 30. The specific target tissue site and the stimulation electrodes used to deliver stimulation to the target tissue site, however, may be selected, e.g., according to the identified patient behaviors and/or other sensed patient parameters. Although leads 38 are shown in FIG. B as being coupled to a common lead extension 36, in other examples, leads 38 may be coupled to IMD 32 via separate lead extensions or directly to connector 34.

In the example shown in FIG. 1B, electrodes 40, 42 of leads 38 are shown as ring electrodes. Ring electrodes may be used in DBS applications because they are relatively simple to program and are capable of delivering an electrical field to any tissue adjacent to electrodes 40, 42. In other examples, electrodes 40, 42 may have different configurations. For example, in some examples, at least some of the electrodes 40, 42 of leads 38 may have a complex electrode array geometry that is capable of producing shaped electrical fields. The complex electrode array geometry may include multiple electrodes (e.g., partial ring or segmented electrodes) around the outer perimeter of each lead 38, rather than one ring electrode. In this manner, electrical stimulation may be directed in a specific direction from leads 38 to enhance therapy efficacy and reduce possible adverse side effects from stimulating a large volume of tissue. External programmer 48 may be similar to programmer 20 of FIG. 1A and wirelessly communicate with IMD 32 as needed to provide or retrieve therapy information.

Figure 2:
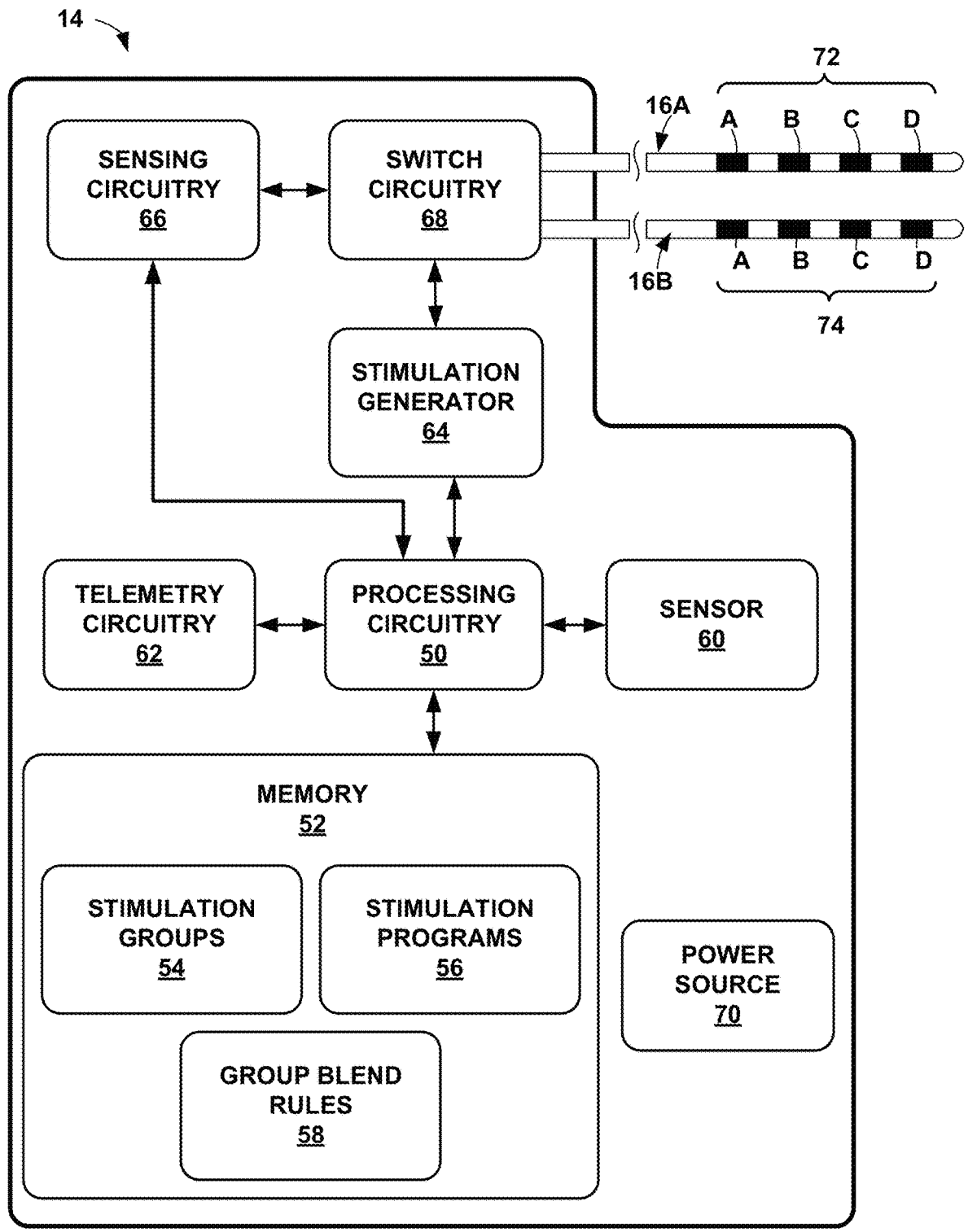
FIG. 2 is a block diagram illustrating example components of an implantable neurostimulator.

FIG. 2 is a block diagram illustrating example components of neurostimulator 14 of FIG. 1A. In the example shown in FIG. 2, neurostimulator 14 includes processing circuitry 50, memory 52, stimulation generator 64, sensing circuitry 66, switch circuitry 68, telemetry circuitry 62, sensor 60, and power source 70. Each of these circuits may be or include programmable or fixed function circuitry configured to perform the functions attributed to respective circuitry. For example, processing circuitry 50 may include fixed-function or programmable circuitry, stimulation generator 64 may include circuitry configured to generate stimulation signals such as pulses or continuous waveforms on one or more channels, sensing circuitry 66 may include sensing circuitry for sensing signals, and telemetry circuitry 62 may include telemetry circuitry for transmission and reception of signals. Memory 52 may store computer-readable instructions that, when executed by processing circuitry 50, cause neurostimulator 14 to perform various functions. Memory 52 may be a storage device or other non-transitory medium. Memory 52 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In the example shown in FIG. 2, memory 52 stores stimulation groups 54, stimulation programs 56, and group blend rules 58 in separate memories within memory 52 or separate areas within memory 52. Each stored stimulation group 54 defines one or more programs, where each program defines respective values for a set of electrical stimulation parameters (e.g., a therapy parameter set), such as a stimulation electrode combination, electrode polarity, current or voltage amplitude, pulse width, pulse rate, and pulse shape. Stimulation programs 56 define the number and duration of each time slot of each set of time slots. In addition, stimulation programs 56 may include instructions on how to determine the duration and number of slots for each set of time slots based on the different programs, groups of programs, or patient criteria. Group blend rules 58 includes instructions that indicate how processing circuitry 50 is to change from one group to the next, such as how many iterations of changes to ratios of programs for each group to use, the number of time slots for each set of time slots, which current pulses in each set of time slots are to be replaced by pulses of one or more programs of the new group in each iteration of the change to the ratios, any other such information.

Accordingly, in some examples, stimulation generator 64 generates electrical stimulation signals in accordance with the electrical stimulation parameters noted above. Other ranges of therapy parameter values may also be useful and may depend on the target stimulation site within patient 12. While stimulation pulses are described, stimulation signals may be of any form, such as continuous-time signals (e.g., sine waves) or the like. Switch circuitry 68 may include one or more switch arrays, one or more multiplexers, one or more switches (e.g., a switch matrix or other collection of switches), or other electrical circuitry configured to direct stimulation signals from stimulation generator 64 to one or more of electrodes 72A-72D and 74A-74D (collectively "electrodes 72, 74"), or directed sensed signals from one or more of electrodes 72, 74 to sensing circuitry 66. In other examples, stimulation generator 64 and/or sensing circuitry 66 may include sensing circuitry to direct signals to and/or from one or more of electrodes 72, 74, which may or may not also include switch circuitry 68.

Processing circuitry 50 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 50 herein may be embodied as firmware, hardware, software or any combination thereof. Processing circuitry 50 controls stimulation generator 64 to generate stimulation signals according to stimulation groups 54 and group blend rules 58 stored in memory 52 to apply stimulation parameter values specified by one or more of programs, such as amplitude, pulse width, pulse rate, and pulse shape of each of the stimulation signals.

In the example shown in FIG. 2, the set of electrodes 72 includes electrodes 72A, 72B, 72C, and 72D, and the set of electrodes 74 includes electrodes 74A, 74B, 74C, and 74D. In other examples, a single lead may include all eight electrodes 72 and 74 along a single axial length of the lead. Processing circuitry 50 also controls stimulation generator 64 to generate and apply the stimulation signals to selected combinations of electrodes 72, 74. In some examples, stimulation generator 64 includes a switch circuit (instead of, or in addition to, switch circuitry 68) that may couple stimulation signals to selected conductors within leads 16, which, in turn, deliver the stimulation signals across selected electrodes 72, 74. Such a switch circuit may be a switch array, switch matrix, multiplexer, or any other type of switching circuit configured to selectively couple stimulation energy to selected electrodes 72, 74 and to selectively sense bioelectrical neural signals of a spinal cord of the patient (not shown in FIG. 2) with selected electrodes 72, 74.

In other examples, however, stimulation generator 64 does not include a switch circuit and switch circuitry 68 does not interface between stimulation generator 64 and electrodes 72, 74. In these examples, stimulation generator 64 comprises a plurality of pairs of voltage sources, current sources, voltage sinks, or current sinks connected to each of electrodes 72, 74 such that each pair of electrodes has a unique signal circuit. In other words, in these examples, each of electrodes 72, 74 is independently controlled via its own signal circuit (e.g., via a combination of a regulated voltage source and sink or regulated current source and sink), as opposed to switching signals between electrodes 72, 74.

Electrodes 72, 74 on respective leads 16 may be constructed of a variety of different designs. For example, one or both of leads 16 may include one or more electrodes at each longitudinal location along the length of the lead, such as one electrode at different perimeter locations around the perimeter of the lead at each of the locations A, B, C, and D. In one example, the electrodes may be electrically coupled to stimulation generator 64, e.g., via switch circuitry 68 and/or switching circuitry of the stimulation generator 64, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form one or more of the leads 16. These and other constructions may be used to create a lead with a complex electrode geometry.

Although sensing circuitry 66 is incorporated into a common housing with stimulation generator 64 and processing circuitry 50 in FIG. 2, in other examples, sensing circuitry 66 may be in a separate housing from neurostimulator 14 and may communicate with processing circuitry 50 via wired or wireless communication techniques.

Sensor 60 may include one or more sensing elements that sense values of a respective patient parameter. Sensor 60 may include one or more accelerometers, optical sensors, chemical sensors, temperature sensors, pressure sensors, or any other types of sensors. Sensor 60 may output patient parameter values that may be used as feedback to control delivery of therapy. For example, sensor 60 may indicate patient activity, and processing circuitry 50 may change the stimulation program based on the current detected patient activity. Neurostimulator 14 may include additional sensors within the housing of neurostimulator 14 and/or coupled via one of leads 16 or other leads. In addition, neurostimulator 14 may receive sensor signals wirelessly from remote sensors via telemetry circuitry 62, for example. In some examples, one or more of these remote sensors may be external to patient (e.g., carried on the external surface of the skin, attached to clothing, or otherwise positioned external to the patient). In some examples, signals from sensor 60 may indicate a position or body state (e.g., sleeping, awake, sitting, standing, or the like).

Telemetry circuitry 62 supports wireless communication between neurostimulator 14 and an external programmer (not shown in FIG. 2) or another computing device under the control of processing circuitry 50. Processing circuitry 50 of neurostimulator 14 may receive, as updates to programs and/or groups of programs, values for various stimulation parameters such as amplitude and electrode combination, from the external programmer via telemetry circuitry 62. Updates to the stimulation groups 54, stimulation programs 56, and/or group blend rules 58 may be stored within memory 52. Telemetry circuitry 62 in neurostimulator 14, as well as telemetry circuits in other devices and systems described herein, such as the external programmer, may accomplish communication by radiofrequency (RF) communication techniques. In addition, telemetry circuitry 62 may communicate with an external medical device programmer (not shown in FIG. 2) via proximal inductive interaction of neurostimulator 14 with the external programmer. Telemetry circuitry 62 may send information to the external programmer on a continuous basis, at periodic intervals, or upon request from neurostimulator 14 or the external programmer.

Power source 70 delivers operating power to various components of neurostimulator 14. Power source 70 may include a rechargeable or non-rechargeable battery and a power generation circuit to produce the operating power. Recharging may be accomplished through proximal inductive interaction between an external charger and an inductive charging coil within neurostimulator 14. In other examples, traditional primary cell batteries may be used.

In one example, the stimulation pulses each have a pulse width of greater than approximately 300 µs and less than approximately 2000 µs (i.e., 2 milliseconds). In some examples, the stimulation pulse width is greater than approximately 300 µs and less than approximately 800 µs. In another example, the stimulation pulse width is greater than approximately 300 µs and less than approximately 500 µs. In one example, stimulation pulses have a pulse width of approximately 450 µs and a pulse frequency of approximately 60 Hertz. Amplitude (current and/or voltage) for the therapy pulses may be between approximately 0.5 mA (or volts) and approximately 10 mA (or volts), although amplitude may be lower or greater in other examples. In other examples, the stimulation pulses may have pulse widths smaller than 300 µs, such as 60 µs or smaller. In other examples, the stimulation pulses may have pulse widths greater than 2000 µs. Moreover, stimulation pulses may have pulse frequencies greater than 100 Hz, greater than 1000 Hz, greater than 5000 Hz, or even greater than 10,000 Hz.

Figure 3:
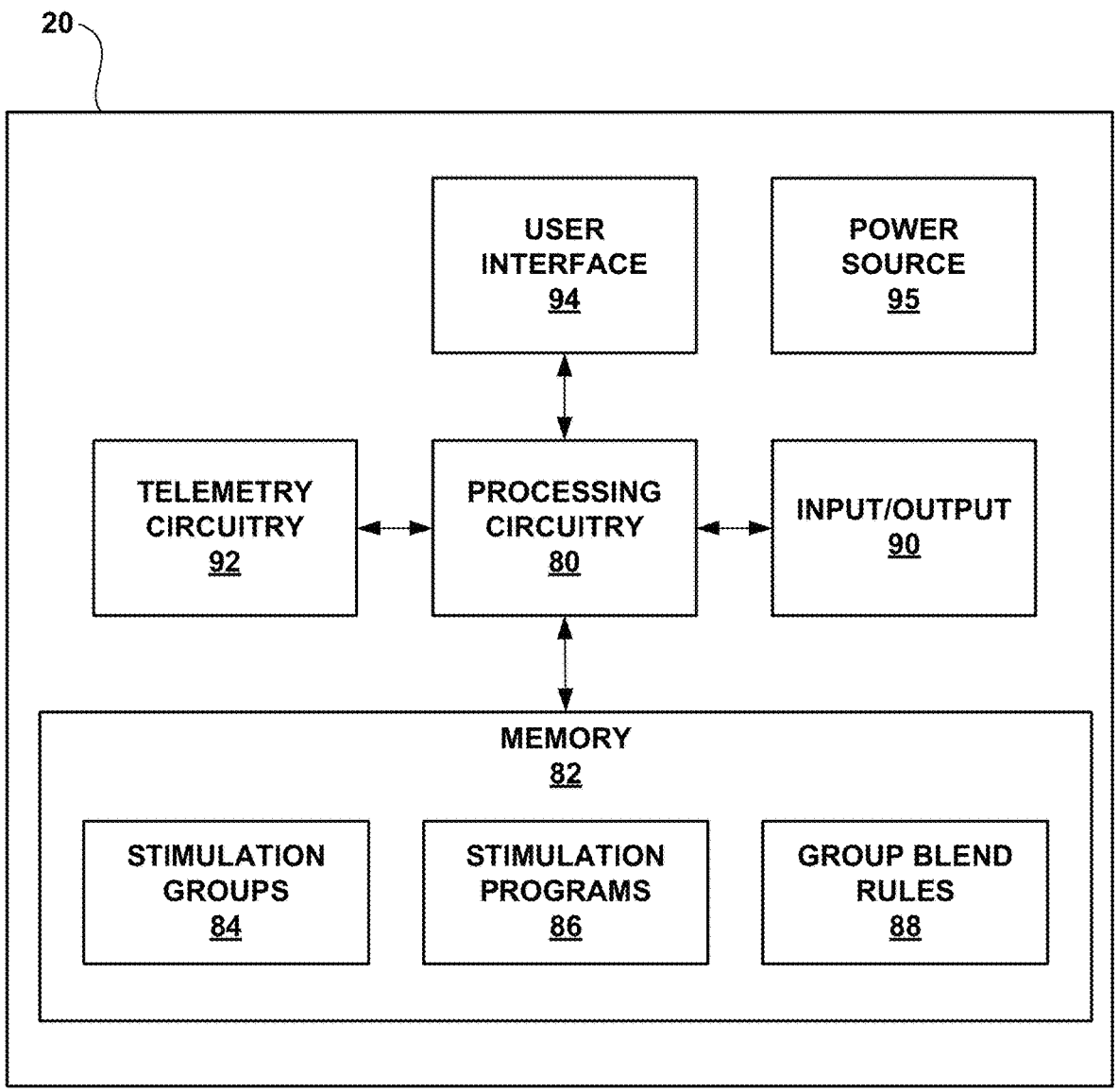
FIG. 3 is a block diagram illustrating example components of an external programmer.

FIG. 3 is a block diagram illustrating example components of external programmer 20. As discussed above, external programmer 20 from FIG. 1A may be similar to programmer 48 of FIG. 1B. Although programmer 20 may generally be described as a hand-held device, programmer 20 may be a larger portable device or a more stationary device. In addition, in other examples, programmer 20 may be included as part of an external charging device or include the functionality of an external charging device. As illustrated in FIG. 3, programmer 20 may include a processing circuitry 80, memory 82, user interface 94, telemetry circuitry 92, input/output 90, and power source 95. Memory 82 may store instructions that, when executed by processing circuitry 80, cause processing circuitry 80 and external programmer 20 to provide the functionality ascribed to external programmer 20 throughout this disclosure. Each of these components, circuitry, or modules, may include electrical circuitry that is configured to perform some, or all of the functionality described herein. For example, processing circuitry 80 may include processing circuitry configured to perform the processes discussed with respect to processing circuitry 80.

In general, programmer 20 comprises any suitable arrangement of hardware, alone or in combination with software and/or firmware, to perform the techniques attributed to programmer 20, and processing circuitry 80, user interface 94, and telemetry circuitry 92 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 82, such as RAM, ROM, PROM, EPROM, EEPROM, flash memory, a hard disk, a CD-ROM, comprising executable instructions for causing the one or more processors to perform the actions attributed to them. Moreover, although processing circuitry 80 and telemetry circuitry 92 are described as separate modules, in some examples, processing circuitry 80 and telemetry circuitry 92 are functionally integrated. In some examples, processing circuitry 80 and telemetry circuitry 92 correspond to individual hardware units, such as ASICs, DSPs, FPGAs, or other hardware units.

Memory 82 (e.g., a storage device) may store instructions that, when executed by processing circuitry 80, cause processing circuitry 80 and programmer 20 to provide the functionality ascribed to programmer 20 throughout this disclosure. For example, memory 82 may store stimulation groups 84, stimulation programs 86, and group blend rules 88, which may be similar to stimulation groups 54, stimulation programs 56, and group blend rules 58 of neurostimulator 14 described in FIG. 2. Programmer 20 may transfer some or all of the instructions stored in stimulation groups 84, stimulation programs 86, and group blend rules 88 to enable functionality regarding blending different groups of programs to neurostimulator 14 to the extent that neurostimulator controls the respective functionality. For example, in some examples, processing circuitry 80 may transmit instructions to neurostimulator 14 to change to a different group (e.g., in response to receiving a user input requesting the different group), and neurostimulator 14 may initiate the change to the new group of programs using the group blend rules 58 stored in memory 52 of neurostimulator 14. Memory 82 may also store data received from a medical device (e.g., neurostimulator 14). For example, memory 82 may store data generated by one or more sensors, such as sensed data related to patient activity and/or posture.

User interface 94 may include a button or keypad, lights, a speaker for voice commands, a display, such as a liquid crystal (LCD), light-emitting diode (LED), or organic light-emitting diode (OLED). In some examples the display may be a touch screen. User interface 94 may be configured to display any information related to the delivery of electrical stimulation, available stimulation programs, available groups of programs, stimulation parameters that may be adjustable, selectable adjustments to group blend rules, or any other information related to stimulation or changing between different groups of programs. User interface 94 may also receive user input via user interface 94. The input may be, for example, in the form of pressing a button on a keypad or selecting an icon from a touch screen. The input may request starting or stopping electrical stimulation, change to a different group of stimulation programs, a slower or faster change to a new group (e.g., a change to the rate of change of the ratio of programs from current and new groups), or other adjustment related to stimulation therapy. In some examples, user interface 94 may provide a button or set of buttons configured to, upon selection by a user, cause processing circuitry 80 to increase or decrease an amplitude of the stimulation pulses currently being delivered to the patient. This change in pulse amplitude may be applied to all pulses delivered during the transition period in some examples. The increase or reduction in amplitude to the pulses may be an absolute voltage or current magnitude, or as a percentage of the current amplitude of the pulses from each program, as a few examples. Input/output 90 may provide a mechanism to receive and/or transmit data via a wired connection with another device.

Telemetry circuitry 92 may support wireless communication between neurostimulator 14 and programmer 20 under the control of processing circuitry 80. Telemetry circuitry 92 may also be configured to communicate with another computing device via wireless communication techniques, or direct communication through a wired connection. In some examples, telemetry circuitry 92 provides wireless communication via an RF or proximal inductive medium. In some examples, telemetry circuitry 92 includes an antenna, which may take on a variety of forms, such as an internal or external antenna.

Examples of local wireless communication techniques that may be employed to facilitate communication between programmer 20 and IMD 14 include RF communication according to the 802.11 or Bluetooth specification sets or other standard or proprietary telemetry protocols. In this manner, other external devices may be capable of communicating with programmer 20 without needing to establish a secure wireless connection. As described herein, telemetry circuitry 92 may be configured to transmit a spatial electrode movement pattern or other stimulation parameter values to IMD 110 for delivery of electrical stimulation therapy.

In some examples, selection of stimulation parameters, stimulation programs, or groups of stimulation programs, may be transmitted to the medical device for delivery to the patient. In other examples, the therapy may include medication, activities, or other instructions that the patient must perform themselves or a caregiver perform for the patient. In some examples, programmer 20 may provide visual, audible, and/or tactile notifications that indicate there are new instructions. Programmer 20 may require receiving user input acknowledging that the instructions have been completed in some examples.

The architecture of programmer 20 illustrated in FIG. 3 is shown as an example. The techniques as set forth in this disclosure may be implemented in the example programmer 20 of FIG. 1A, as well as other types of systems not described specifically herein. Nothing in this disclosure should be construed so as to limit the techniques of this disclosure to the example architecture illustrated by FIG. 3.

FIG. 4 is a conceptual diagram illustrating an example set of time slots 100 within which a respective stimulation pulse may be delivered. As shown in FIG. 4, set of time slots 100 includes four respective time slots 102A, 102B, 102C, and 102D (collectively "time slots 102"). Each time slot of time slots 102 has a duration, or width, W which defines the time during which up to one stimulation pulse may be delivered (e.g., no pulses or a single pulse). Generally, each time pulse of time pulses 102 has the same duration W. The period P indicates the duration of time for the entire set of time pulses 100. In some examples, the period P may have a duration of anywhere from approximately 10 microseconds (μs) to 655,350 μs, but other durations are also possible. Therefore, the width W may be selected as a fraction of the period P. For example, when each period includes four slots, the width W may be a fourth of the duration of the period P. As discussed herein, the period P and/or the width W may be selected to accommodate the pulse width and pulse frequency of the pulses defined by any programs that will be used to deliver therapy within the period P (e.g., programs from one or more groups of programs).

Each time slot of time slots 102 provide a duration in time during which a stimulation pulse may be delivered. Therefore, successive time slots to the right come later in time. For example, time slot 102B represents a duration of time immediately after time slot 102A. Neurostimulator 14 may deliver pulses defined by a current group of programs in some or all of time slots 102 when neurostimulator 14 is delivering therapy according only to the current group. However, when neurostimulator 14 is changing stimulation from the current group to a new group, neurostimulator 14 may place pulses defined by programs from either the current group or the next group in one or more time slots of time slots 102. The number of programs from each group that are used to define pulses delivered during set of time slots 100 indicates the ratio, or percentage, of programs from each group during the period P. As described herein, processing circuitry 50 of neurostimulator 14 may change this ratio of programs from each group in a subsequent set of time slots in order to continue to transition from one group to another group. In some examples, neurostimulator 14 may keep the same ratio of programs used to define pulses over two or more consecutive set of time slots.

The duration W of each time slot of time slots 102 may be a predetermined value. In other examples, processing circuitry 50 may change the duration W for the time slots of a set of time slots based on the parameters of the pulses defined by the one or more programs from each respective group involved in the transition. For example, processing circuitry 50 may set the duration W to handle pulses of different pulse width and/or different pulse frequency between programs from the two groups. In this manner, processing circuitry 50 may set the duration W to have duration that enables a common pulse rate shared between the pulses of programs from both groups. For example, processing circuitry 50 may set the duration W to be a width that allows a single simulation pulse from a first program of a first group defining a faster pulse rate than a second program from a second group to be delivered in a single time slot and pulses from the second program with a slower pulse rate to be delivered in respective time slots. In some examples, this change in duration W may result in time slots in which no pulses are delivered in order to maintain the different pulse frequencies from each of the different programs from the different respective groups.

Although four time slots 102 are shown in the example of FIG. 4, each set of time slots 100 may have a different number of time slots. For example, a set of time slots may have as few as 1 time slot or as many as 6, 8, 10, 20, or even more time slots. Processing circuitry 50 may also select the number of time slots in each set of time slots according to the differences in pulse frequency between the different programs from each group of programs in order to provide the common pulse rate for the different pulses. The entire transition period over which processing circuitry 50 completely changes from one group to another group may include two or more sets of time slots. The greater number of sets of time slots may facilitate more gradual changes to the ratios of programs from each of the different groups over the transition period.

As described herein, a single stimulation pulse may be delivered during each time slot of time slots 102. A single stimulation pulse may include both the stimulation phase and the recharge phase of the pulse. The stimulation phase may have an opposite polarity from the recharge phase. In some examples, the stimulation pulse may include three or more phases, such as two stimulation phases and one recharge phase. In any case, the total charge delivered from one or more stimulation phases may be approximately equal and opposite the total charge delivered during the one or more recharge phases. In other examples, only the stimulation phase may be delivered during a single time slot, and a corresponding recharge phase may follow one or more stimulation phases delivered during respective time slots. In this manner, the recharge phase may be delivered during its own time slot in some examples. Although time slots 102 are described has containing none or only a single stimulation pulse, multiple pulses may be delivered within a single time slot in other examples.

Although time slots are described herein as an example technique to manage pulse delivery from one or more programs of respective groups of programs, other techniques may be used in other examples. For example, processing circuitry 50 may simply track the number of pulses from each program of a group of programs over a specified period of time and adjust the number of programs from each group to change the ratio of programs from the group used to define pulses over this specified period of time during the transition period. In other examples, processing circuitry 50 may count pulses from each of the programs of a group and adjust the number of programs from a group of programs that define respective pulses over time without respect to how much time elapses between each change of the ratio of programs from each different group. For example, processing circuitry 50 may deliver four pulses according to four programs from a first group of programs, followed by a single pulse according to a program from a second group of programs, followed by three pulses according to three programs from the first group of programs, followed by two pulses according to two programs from the second group of programs, and continue this process until processing circuitry 50 is only controlling neurostimulator 14 to deliver pulses defined by programs from the second group of programs.

Figure 5:
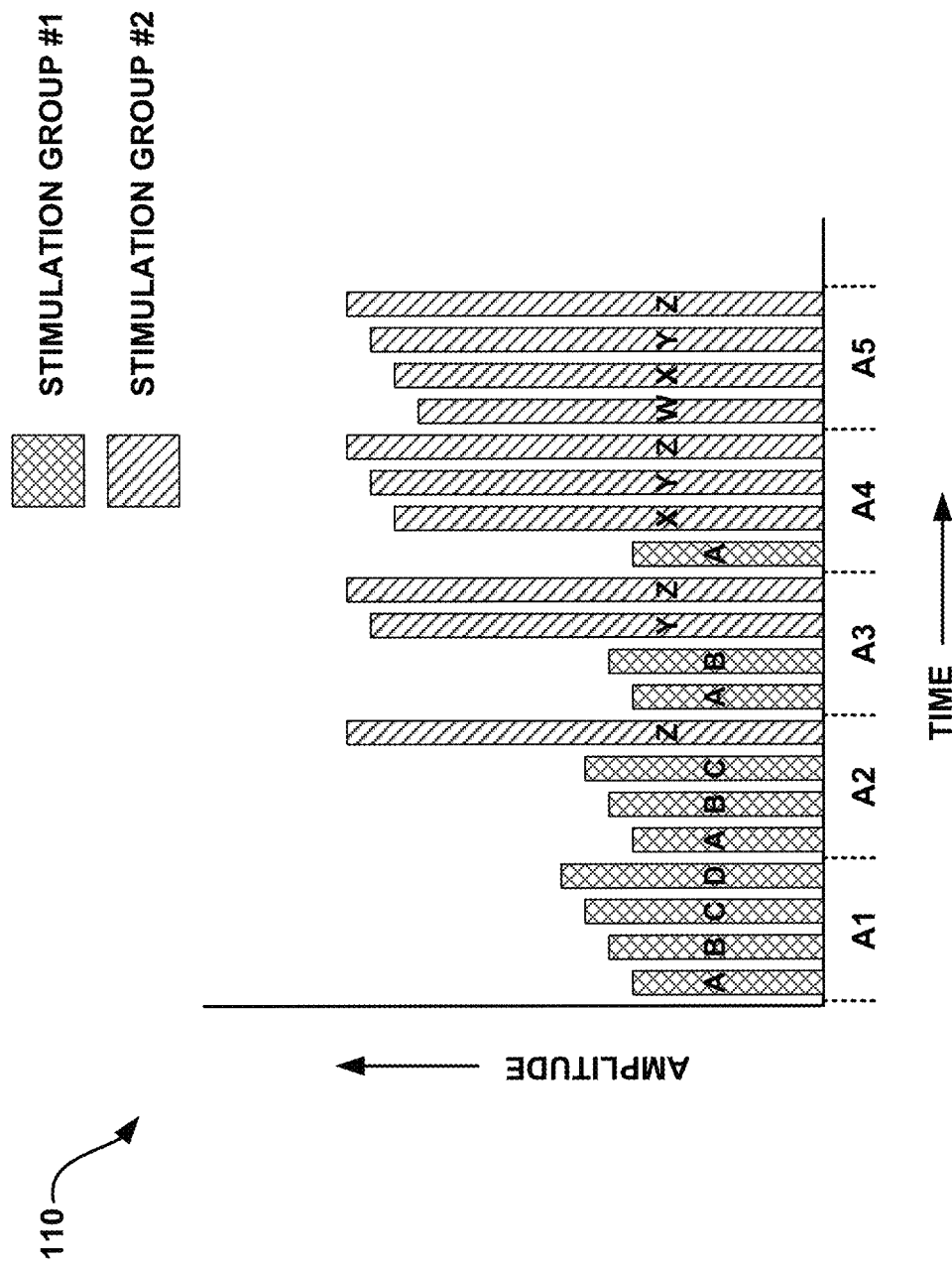
FIGS. 5, 6, and 7 are timing diagrams of example changes to ratios of programs from different groups of programs that define pulses during a transition period.
Figure 6:
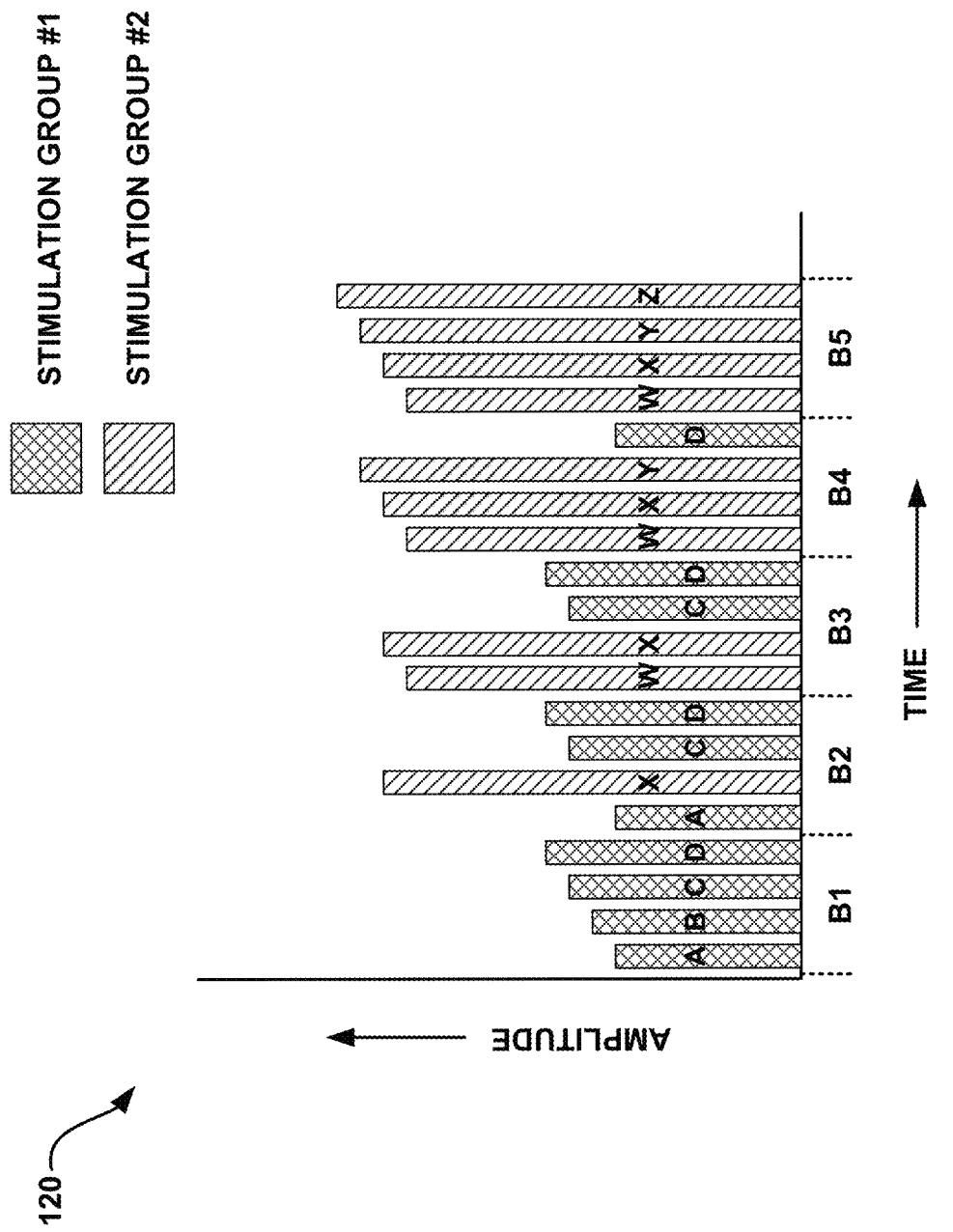
Figure 7:
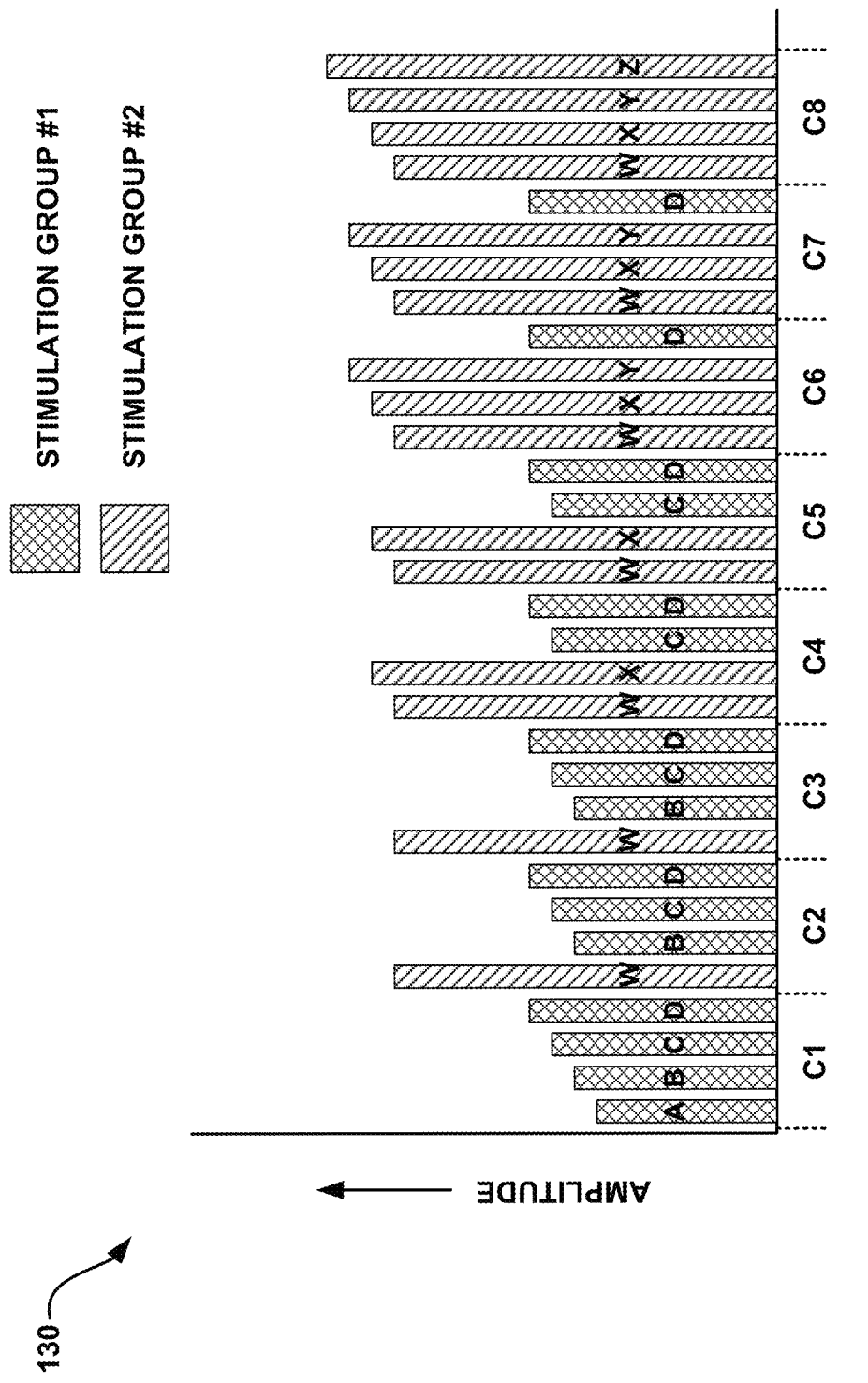

FIGS. 5, 6, and 7 are timing diagrams of example changes to ratios of programs from different groups of programs used to define pulses during a transition period. Processing circuitry 50 of neurostimulator 14 will be described with respect to FIGS. 5, 6, and 7, but similar functionality may be provided by other devices or processing circuitry, and may include a programmer such as programmer 20 in some examples. As shown in FIG. 5, timing diagram 110 includes periods A1, A2, A3, A4, and A5 which correspond to the period of time for each respective set of time slots (e.g., different sets 100 of time slots), where each set of time slots includes four time slots. Processing circuitry 50 may determine which pulses from which programs of each group of programs (e.g., stimulation group 1 or stimulation group 2) should be delivered in each time slot. In the example of FIG. 5, group 1 and group 2 each include different programs which are shown to have different amplitudes to facilitate illustration of the change in the programs used to deliver each pulse. In addition, all programs from group 2 define pulses of greater amplitude than all programs from group 1 for ease of illustration. However, in other examples, each respective program may be different from any other program by one or more parameters, not just amplitude. In addition, as shown in the example of FIG. 5, each of groups 1 and 2 include four respective programs (e.g., eight different programs in total between both of groups 1 and 2). However, a group of stimulation programs may have different numbers of programs and as few as a single program in other examples.

In A1, processing circuitry 50 provides respective pulses defined by each of programs A, B, C, and D from group 1 in each of the four time slots because the transition period has not yet begun. In this manner, group 1 is the current group of stimulation programs, or the first group of stimulation programs. A2 is the first set of time slots of the transition period, where the transition period includes A2, A3, and A4. The first three time slots include pulses defined by programs A, B, and C from group 1, and the fourth and last time slot includes a pulse defined by program Z of different group 2. In the next period of time of the transition period, A3 shows that pulses defined by programs A and B of group 1 are delivered in the first two time slots and pulses defined by programs Y and Z of group 2 are delivered in the last two time slots. In this manner, processing circuitry 50 has changed the ratio of programs from each of group 1 and group 2 used to define pulses in A2 (e.g., 3:1) to a different ratio of programs from each of group 1 and group 2 used to define pulses in A3 (e.g., 1:1). Again, processing circuitry 50 changes the ratio of programs from each of group 1 and group 2 used to define pulses in A4 to 1:3, such that an increasing number of programs from group 2 define pulses over the transition period. In A5, the transition period has ended because all of the pulses in the time slots of A5 are defined by respective programs W, X, Y, and Z of group 2.

Although processing circuitry 50 has placed the new pulses defined by programs from group 2 at the end of each set of time slots, processing circuitry 50 may take a different approach in other situations. For example, processing circuitry 50 may start the transition period by placing a pulses defined by one or more program of group 2 in the first time slot of A2, the first two time slots of A3, and the first three time slots of A4. Although A2, A3, and A4 are described to be part of the transition period, A1 and A5 may also be considered part of the transition period in some examples because the ratio of programs from each group that defines pulses changes from A1 to A2 and from A4 to A5. It is noted that group 1 and group 2 may be different due to programs that have different values of parameters other than amplitude, such as having a different pulse width, pulse frequency, and/or electrode combination.

FIG. 6 shows timing diagram 120 that includes periods B1, B2, B3, B4, and B5 correspond to the period of time for each respective set of time slots (e.g., different sets of 100 time slots), where each set of time slots includes four time slots, similar to the example of FIG. 5. However, in the timing diagram of 120, processing circuitry 50 has randomized the placement of pulses from respective programs of each of group 1 and group 2 from one set of time slots to the next.

In set of time slots B1, processing circuitry 50 provides pulses defined by respective programs A, B, C, and D from group 1 in each of the four time slots because the transition period has not yet begun. B2 is the first set of time slots of the transition period, where the transition period includes B2, B3, and B4. The first, third, and fourth time slots in B2 include a respective pulse defined by programs A, C, and D of group 1, and the second time slot includes a pulse defined by program X of group 2. In the next period of time of the transition period, B3 shows that pulses defined by programs C and D from group 1 are delivered in the third and fourth time slots, and pulses defined by programs W and X from group 2 are delivered in the first and second time slots. In this manner, processing circuitry 50 has changed the ratio of programs from group 1 and group 2 that deliver pulses in B2 (e.g., 3:1) to a different ratio of programs from group 1 and group 2 in B3 (e.g., 1:1). However, processing circuitry 50 has randomized the position of pulses defined by respective programs from each group within the different sets of time slots. Processing circuitry 50 then changes the ratio of programs from group 1 and group 2 that define pulses in B4 to 1:3, where the first three time slots include pulses defined programs W, X, and Y from group 2, and the last time slot includes a pulse defined by program D of group 1. In B5, the transition period has ended because all of the pulses in the time slots of B5 are defined by programs W, X, Y, and Z of group 2. The placement of pulses defined by respective programs from group 1 and 2 may be completely random, pseudo random, or varied between different sets of time slots according to an algorithm intended to merely switch the positions of pulses from respective programs during the transition period.

FIG. 7 shows timing diagram 130, which may be similar to timing diagrams 110 and 120 of FIGS. 5 and 6. However, timing diagram 130 illustrates that processing circuitry 50 may maintain the ratio of programs from each of group 1 and group 2 defining pulses between consecutive sets of time slots during the transition period. Timing diagram 30 includes periods C1, C2, C3, C4, C5, C6, C7, and C8 which correspond to the period of time for each respective set of time slots (e.g., different sets of 100 time slots), where each set of time slots includes four time slots, although other numbers of time slots may be used in other examples. Although processing circuitry 50 has placed the new pulses defined by programs from group 2 at the beginning of each set of time slots, processing circuitry 50 may place the new pulses defined by programs from group 2 in other time slots of the set in other examples.

In set of time slots C1, processing circuitry 50 provides pulses defined by programs A, B, C, and D from group 1 in each of the four time slots because the transition period has not yet begun. C2 is the first set of time slots of the transition period, where the transition period includes C2-C7. The first time slot of C2 includes a pulse defined by program W from group 2, and the second, third, and fourth time slots of C2 include pulses defined by programs B, C, and D of group 1, respectively. Instead of changing the ratio of programs from group 1 and group 2 defining pulses between C2 and C3, processing circuitry 50 maintains the ratio of programs and the position of respective pulses from each program of each group. In other examples, processing circuitry 50 may maintain the ratio of programs between sets of time slots while changing the position of the pulses from each program of each group. Then, processing circuitry 50 changes the ratio of programs from group 1 and group 2 that define pulses between C3 and C4.

Processing circuitry 50 may maintain the ratio of programs from each of groups 1 and 2 between periods C2 and C3, C4 and C5, and C6 and C7. However, processing circuitry 50 may change the ratio of programs from each group defining pulses between periods C1 and C2, C3 and C4, C5 and C6, and C7 and C8. By maintaining the ratio of programs from each group between two or more sets of time slots, processing circuitry 50 may slow down the rate at which stimulation changes from group 1 to group 2. For example, the switch from group 1 to group 2 is performed over seven sets of time slots in FIG. 7 as compared to only 4 sets of time slots in FIGS. 5 and 6.

Although processing circuitry 50 is described as generally increasing or maintaining the ratio of the programs from the next groups of programs used to define pulses over the course of the transition period, other approaches are contemplated. For example, processing circuitry 50 may decrease the ratio of programs from the next group (e.g., group 2) to the current group (e.g., group 1) one or more times during the transition period. This reduction in programs from the next group used to define pulses at one or more times during the transition period may provide a more comfortable or acceptable change to stimulation for some patients.

FIGS. 8A and 8B are graphs of example blending of different groups of stimulation programs. FIG. 8A provides graph 140 which shows an overview of the change between three different groups (referred to as Group A, B, and C while discussing FIGS. 8A and 8B) of programs to generate the pulse trace 142. FIG. 8B is a more detailed view of the transition from Group A to Group B that define pulses 144 and 146. As shown in FIG. 8A, pulse trace 142 indicates that pulses 143 are delivered solely according to Group A programs. Pulses 144 and 146 indicate the transition period during which pulses are delivered according to programs from both Group A and Group B. Pulses 144 show the change in group rate followed by pulses 146 showing the ratios of the programs transitioning after each successive rate period from Group A to Group B. Pulses 148 show a period of static (non-changing) pulses as defined solely by Group B. Pulses 150 and 152 show the transition period during which pulses are delivered according to programs from both Group B and Group C. Pulses 150 show the change in group rate followed by pulses 152 showing the ratios of the programs transition after each successive rate period from Group B to Group C. Pulses 154 show pulses with a settling period solely under the control of Group C. The drift in amplitude shown in pulses 146 may be due to residual electrical charge in tissue which takes some time to dissipate as the pulses are delivered.

As shown in FIG. 8B, a more detailed view of pulses 144 and pulses 146 is provided to show the blending of the programs from Group A with programs from Group B. It is noted that pulses defined by the programs within each group respectively, have a common setting for each of the parameter values (rate, amplitude, pulse width, electrode contacts and polarity) for purposes of illustration. However, each program of a group may define one or more different parameter values from the other programs in the group. It is also noted that in this example there are four programs for each group and therefore there are four time slots within each rate period with one program allocated to a given time slot. Graph 160 shows that pulses 144 mark the beginning of the transition from Group A to Group B with the change in pulse rate. At the beginning of pulse train 146, in the first five rate periods the transition of the first program from a positive to negative polarity can be seen while the other three programs (slots positions) are still operating from the parameters of Group A with positive polarities (refer to the third rate period as depicted with pulses 162). So the waveform first shows one program transitioned to negative polarity in the first five rate periods of pulses 146. Then by the sixth rate period another program had transitioned to negative polarity (Group B control). This pattern of transitioning each program, one by one continues until all are operating under Group B control.

Figure 9:
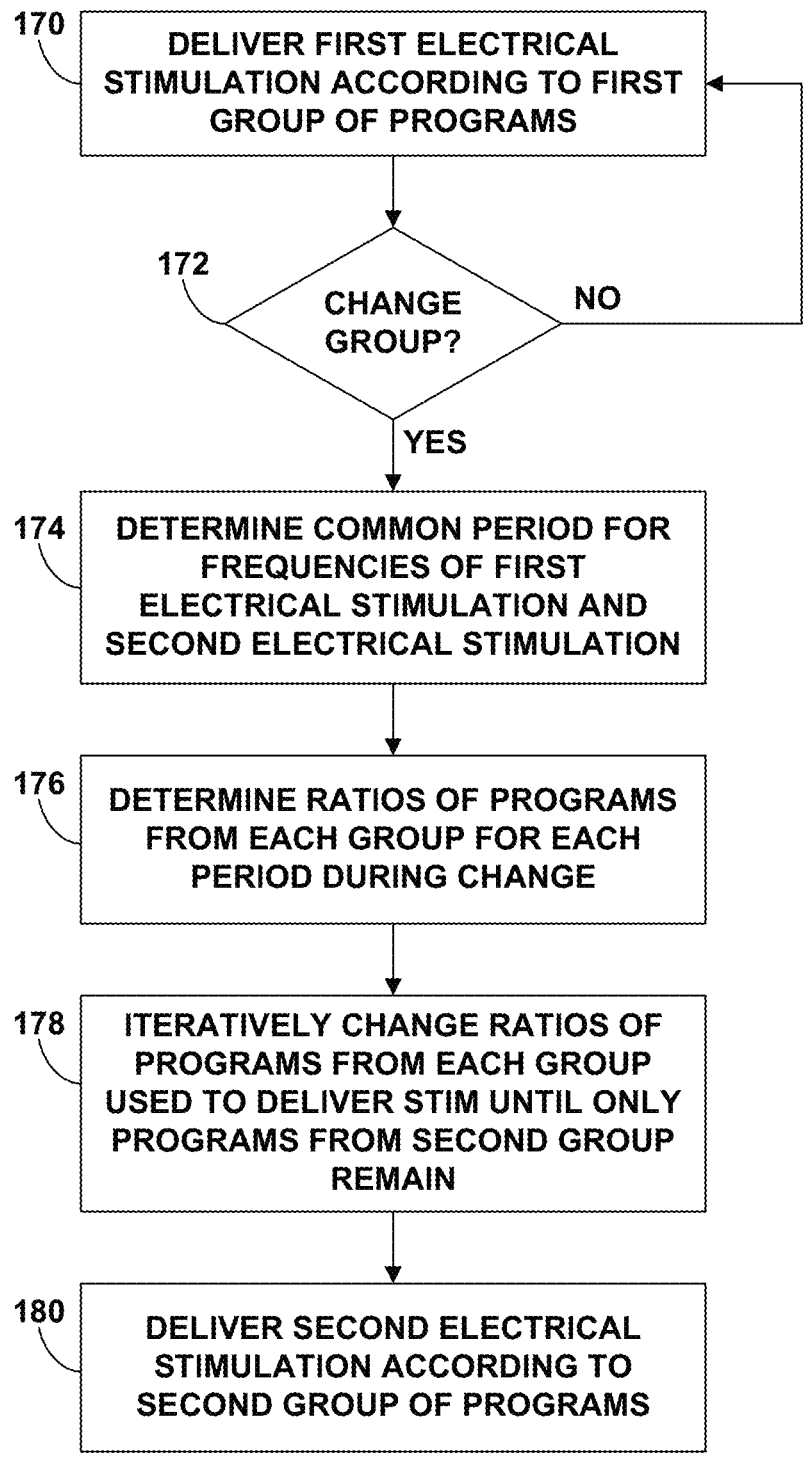
FIG. 9 is a flow diagram of an example technique for transitioning between two different stimulation programs.

FIG. 9 is a flow diagram of an example technique for transitioning between two different groups of stimulation programs. The example of FIG. 9 will be described with respect to processing circuitry 50 and stimulation generator 64 of neurostimulator 14. However, other components or devices, or combinations thereof, may also provide similar functionality, such as processing circuitry 80 of programmer 20.

As shown in FIG. 9, processing circuitry 50 controls stimulation generator 64 to deliver first electrical stimulation according to a first group of stimulation program (170). If processing circuitry 50 is not instructed to change the group ("NO" branch of block 172), processing circuitry 50 may continue to deliver the first electrical stimulation therapy (170). If processing circuitry 50 is instructed to change the group ("YES" branch of block 172), processing circuitry 50 determines a common period for the frequencies of the first electrical stimulation defined by programs of the first group of programs and second electrical stimulation defined by programs of a second group of programs (174). For example, processing circuitry 50 may calculate a period for each time slot of a set of time slots that will accommodate pulses according to the pulse frequency of programs the first group and the pulse frequency of programs of the second group. In other examples, processing circuitry 50 may continue to use a predetermined period for the time slots.

Then, processing circuitry 50 determines the ratios of the programs from each group that will define stimulation for each period (e.g., the period of a set of time slots) during the transition period when changing from the first group of programs to the second group of programs (176). Processing circuitry 50 may determine these ratios according to group blend rules 58, for example. Processing circuitry 50 then iteratively changes the ratios of the programs from each group that define stimulation pulses for different periods of time during the transition period until only pulses defined by programs of the second group of programs are delivered (178). As described herein, the ratio of programs from each group used to define stimulation may change during each period or be maintained between at least some of the periods during the transition period. Then, processing circuitry 50 continues to deliver second electrical stimulation pulses according to the programs of the second group of programs (180).

In some examples, processing circuitry 50 may need to change to a third group of programs during the transition period between the first and second groups. This third group of programs may be specified based on sensed data identified by processing circuitry 50 and/or a request from the user via programmer 20. In this case, processing circuitry 50 may begin to transition to the third group while also delivering pulses from one or more programs of the first and second groups of programs. For example, processing circuitry 50 may begin to add pulses from one or more program of the third group in place of pulses defined by one or more programs from the first and/or second group such that the pulses defined by the third group of programs eventually replace all of the pulses from the programs of the first and/or second group. During this transition period, a set of time slots may include pulses from all of the first, second, and third groups or pulses from the second and third groups. In other examples, processing circuitry 50 may complete the transition from the first group to the second group before transitioning from the second group to the third group.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
controlling, by processing circuitry, delivery of first electrical stimulation defined by two or more first programs of a first group of stimulation programs;
controlling, by the processing circuitry, delivery of second electrical stimulation defined by two or more second programs of a second group of stimulation programs on a time-interleaved basis with the first electrical stimulation defined by the two or more first programs of the first group of stimulation programs, wherein at least one program of the two or more first programs defines at least one stimulation parameter value different from at least one stimulation parameter value defined by at least one program of the two or more second programs; and
changing, by the processing circuitry, a first ratio of the two or more first programs used to define the first electrical stimulation to the two or more second programs used to define the second electrical stimulation delivered within a first period of time to a second ratio of the two or more first programs used to define the first electrical stimulation to the two or more second programs used to define the second electrical stimulation delivered within a second period of time.

2. The method of claim 1, wherein changing the first ratio of the two or more first programs used to define the first electrical stimulation to the two or more second programs used to define the second electrical stimulation within the first period of time to the second ratio of the two or more first programs used to define the first electrical stimulation to the one or more programs used to define the second electrical stimulation delivered within the second period of time comprises increasing a number of the two or more second programs used to define the second electrical stimulation delivered during the second period of time as compared to the first period of time.

3. The method of claim 2, wherein changing the first ratio of the two or more first programs used to define the first electrical stimulation to the two or more second programs used to define the second electrical stimulation delivered within the first period of time to the second ratio of the two or more first programs used to define the first electrical stimulation to the two or more second programs used to define the second electrical stimulation delivered within the second period of time comprises decreasing a number of the two or more first programs used to define the first electrical stimulation delivered during the second period of time compared to the first period of time.

4. The method of claim 1, wherein changing the first ratio of the two or more first programs used to define the first electrical stimulation to the two or more second programs used to define the second electrical stimulation delivered within the first period of time to the second ratio of the two or more first programs used to define the first electrical stimulation to the two or more second programs used to define the second electrical stimulation delivered within the second period of time comprises decreasing a number of the two or more first programs used to define the first electrical stimulation delivered during the second period of time as compared to the first period of time.

5. The method of claim 1, wherein:
controlling the delivery of the first electrical stimulation comprises controlling delivery of at least one pulse of the first electrical stimulation within the second period of time; and
controlling the delivery of the second electrical stimulation comprises controlling delivery of at least one pulse of the second electrical stimulation within the second period of time.

6. The method of claim 1, wherein controlling the delivery of the second electrical stimulation on the time-interleaved basis with the first electrical stimulation comprises controlling the delivery of a first set of one or more pulses of the first electrical stimulation alternating with a second set of one or more pulses of the second electrical stimulation.

7. The method of claim 1, wherein each of the first period of time and the second period of time comprises a plurality of time slots, each time slot of the plurality of time slots being configured to contain up to a single stimulation pulse from one of at least the first electrical stimulation defined by the two or more first programs or the second electrical stimulation defined by two or more second programs.

8. The method of claim 7, wherein a duration of the plurality of time slots correspond to a common pulse rate period shared between the first electrical stimulation defined by the two or more first programs and the second electrical stimulation defined by two or more second programs.

9. The method of claim 7, wherein the plurality of time slots comprises at least four time slots having equal lengths.

10. The method of claim 7, wherein the single stimulation pulse comprises a stimulation phase and a recharge phase.

11. The method of claim 1, further comprising iteratively changing the second ratio of the two or more first programs used to define the first electrical stimulation to the two or more second programs used to define the second electrical stimulation delivered on the second time-interleaved basis within the second period of time to one or more subsequent ratios of a decreasing number of the two or more first programs used to define the first electrical stimulation to an increasing number of the two or more second programs used to define the second electrical stimulation delivered on subsequent time-interleaved bases within subsequent period of times until the first electrical stimulation is no longer delivered.

12. The method of claim 1, further comprising changing a first order of the two or more first programs used to define the first electrical stimulation and the two or more second programs used to define the second electrical stimulation delivered within the first period of time to a second order of the two or more first programs used to define the first electrical stimulation and the two or more second programs used to define the second electrical stimulation delivered within a third period of time.

13. The method of claim 1, further comprising controlling delivery of third electrical stimulation defined by two or more third programs of a third group of stimulation programs on the time-interleaved basis with the first electrical stimulation defined by the two or more first programs and the second electrical stimulation defined by the two or more second programs within at least one of the first period of time or the second period of time.

14. The method of claim 1, wherein each of the two or more first programs and each of the two or more second programs define a respective set of stimulation parameters comprising at least one of an amplitude, a pulse rate, a pulse width, an electrode combination, or an electrode polarity.

15. The method of claim 1, further comprising:
delivering, by an implantable medical device, the first electrical stimulation; and
delivering, by the implantable medical device, the second electrical stimulation.

16. A system comprising:
processing circuitry configured to:
control delivery of first electrical stimulation defined by two or more first programs of a first group of stimulation programs;
control delivery of second electrical stimulation defined by two or more second programs of a second group of stimulation programs on a time-interleaved basis with the first electrical stimulation defined by the two or more first programs of the first group of stimulation programs, wherein at least one program of the two or more first programs defines at least one stimulation parameter value different from at least one stimulation parameter value defined by at least one program of the two or more second programs; and
change a first ratio of the two or more first programs used to define the first electrical stimulation to the two or more second programs used to define the second electrical stimulation delivered within a first period of time to a second ratio of the two or more first programs used to define the first electrical stimulation to the two or more second programs used to define the second electrical stimulation delivered within a second period of time.

17. The system of claim 16, wherein the processing circuitry is configured to change the first ratio of the two or more first programs used to define the first electrical stimulation to the two or more second programs used to define the second electrical stimulation within the first period of time to the second ratio of the two or more first programs used to define the first electrical stimulation to the two or more programs used to define the second electrical stimulation delivered within the second period of time by increasing a number of the two or more second programs used to define the second electrical stimulation delivered during the second period of time as compared to the first period of time.

18. The system of claim 17, wherein the processing circuitry is configured to change the first ratio of the two or more first programs used to define the first electrical stimulation to the two or more second programs used to define the second electrical stimulation delivered within the first period of time to the second ratio of the two or more first programs used to define the first electrical stimulation to the two or more second programs used to define the second electrical stimulation delivered within the second period of time by decreasing a number of the two or more first programs used to define the first electrical stimulation delivered during the second period of time compared to the first period of time.

19. The system of claim 16, wherein the processing circuitry is configured to change the first ratio of the two or more first programs used to define the first electrical stimulation to the two or more second programs used to define the second electrical stimulation delivered within the first period of time to the second ratio of the two or more first programs used to define the first electrical stimulation to the two or more second programs used to define the second electrical stimulation delivered within the second period of time by decreasing a number of the two or more first programs used to define the first electrical stimulation delivered during the second period of time as compared to the first period of time.

20. The system of claim 17, wherein the processing circuitry is configured to:
control the delivery of the first electrical stimulation comprises controlling delivery of at least one pulse of the first electrical stimulation within the second period of time; and
control the delivery of the second electrical stimulation comprises controlling delivery of at least one pulse of the second electrical stimulation within the second period of time.

21. The system of claim 16, wherein the processing circuitry is configured to control the delivery of the second electrical stimulation on the time-interleaved basis with the first electrical stimulation by controlling the delivery of a first set of one or more pulses of the first electrical stimulation alternating with a second set of one or more pulses of the second electrical stimulation.

22. The system of claim 16, wherein each of the first period of time and the second period of time comprises a plurality of time slots, each time slot of the plurality of time slots being configured to contain up to a single stimulation pulse from one of at least the first electrical stimulation defined by the two or more first programs or the second electrical stimulation defined by two or more second programs.

23. The system of claim 22, wherein a duration of the plurality of time slots correspond to a common pulse rate period shared between the first electrical stimulation defined by the two or more first programs and the second electrical stimulation defined by two or more second programs.

24. The system of claim 22, wherein the plurality of time slots comprise at least four time slots having equal lengths.

25. The system of claim 22, wherein the single stimulation pulse comprises a stimulation phase and a recharge phase.

26. The system of claim 16, wherein the processing circuitry is configured to iteratively change the second ratio of the two or more first programs used to define the first electrical stimulation to the two or more second programs used to define the second electrical stimulation delivered on the second time-interleaved basis within the second period of time to one or more subsequent ratios of a decreasing number of the two or more first programs used to define the first electrical stimulation to an increasing number of the two or more second programs used to define the second electrical stimulation delivered on subsequent time-interleaved bases within subsequent period of times until the first electrical stimulation is no longer delivered.

27. The system of claim 16, wherein the processing circuitry is configured to change a first order of the two or more first programs used to define the first electrical stimulation and the two or more second programs used to define the second electrical stimulation delivered within the first period of time to a second order of the two or more first programs used to define the first electrical stimulation and the two or more second programs used to define the second electrical stimulation delivered within a third period of time.

28. The system of claim 16, wherein the processing circuitry is configured to control delivery of third electrical stimulation defined by two or more third programs of a third group of stimulation programs on the time-interleaved basis with the first electrical stimulation defined by the two or more first programs and the second electrical stimulation defined by the two or more second programs within at least one of the first period of time or the second period of time.

29. The system of claim 16, wherein each of the two or more first programs and each of the two or more second programs define a respective set of stimulation parameters comprising at least one of an amplitude, a pulse rate, a pulse width, an electrode combination, or an electrode polarity.

30. The system of claim 16, further comprising an implantable medical device configured to:
deliver the first electrical stimulation; and
deliver the second electrical stimulation.

31. A non-transitory computer-readable medium comprising instructions that, when executed, cause processing circuitry to:
control delivery of first electrical stimulation defined by two or more first programs of a first group of stimulation programs;
delivery of second electrical stimulation defined by two or more second programs of a second group of stimulation programs on a time-interleaved basis with the first electrical stimulation defined by the two or more first programs of the first group of stimulation programs, wherein at least one program of the two or more first programs defines at least one stimulation parameter value different from at least one stimulation parameter value defined by at least one program of the two or more second programs; and
change a first ratio of the two or more first programs used to define the first electrical stimulation to the two or more second programs used to define the second electrical stimulation delivered within a first period of time to a second ratio of the two or more first programs used to define the first electrical stimulation to the two or more second programs used to define the second electrical stimulation delivered within a second period of time.

* * * * *